(12) United States Patent
Shigemori et al.

(10) Patent No.: US 8,439,822 B2
(45) Date of Patent: May 14, 2013

(54) CAPSULE ENDOSCOPE

(75) Inventors: Toshiaki Shigemori, Hachioji (JP);
Tatsuya Orihara, Hachioji (JP);
Hidetake Segawa, Hachioji (JP);
Hironao Kawano, Machida (JP); Ayako Nagase, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1023 days.

(21) Appl. No.: 12/471,985

(22) Filed: May 26, 2009

(65) Prior Publication Data
US 2009/0299144 A1    Dec. 3, 2009

Related U.S. Application Data

(63) Continuation of application No. PCT/JP2007/066799, filed on Aug. 29, 2007.

(30) Foreign Application Priority Data

Nov. 24, 2006    (JP) ............................... 2006-317684

(51) Int. Cl.
*A61B 1/00*    (2006.01)
*A61B 1/06*    (2006.01)
(52) U.S. Cl.
USPC ........................................ 600/103; 600/160
(58) Field of Classification Search ................. 600/103, 600/109, 117, 118, 160
See application file for complete search history.

(56) References Cited

U.S. PATENT DOCUMENTS

| 6,689,056 | B1 * | 2/2004 | Kilcoyne et al. ............. 600/300 |
| 2003/0171652 | A1 | 9/2003 | Yokoi et al. |
| 2004/0225223 | A1 * | 11/2004 | Honda et al. .................. 600/476 |
| 2006/0004255 | A1 * | 1/2006 | Iddan et al. .................... 600/160 |
| 2006/0056828 | A1 * | 3/2006 | Iddan et al. ...................... 396/14 |

(Continued)

FOREIGN PATENT DOCUMENTS

| JP | 2003-210394 A | 7/2003 |
| JP | 2003-325441 | 11/2003 |

(Continued)

OTHER PUBLICATIONS

Extended Supplementary European Search Report dated Feb. 9, 2010.

(Continued)

*Primary Examiner* — Philip R Smith
(74) *Attorney, Agent, or Firm* — Scully Scott Murphy & Presser, PC

(57) ABSTRACT

A capsule endoscope includes a capsule-shaped casing and an imaging unit for taking an image of an inside of an organ in a state where the capsule endoscope is floating in liquid introduced inside the organ of a subject. Specific gravity of the capsule endoscope to the introduced liquid is ρ; a plane divides the capsule endoscope such that a volume ratio is to be ρ:1−ρ. A straight line that connects a center of volume of a portion whose volume ratio is ρ and a center of gravity of the capsule endoscope is substantially perpendicular to the plane. The center of gravity is present at a position farther distant from the plane than the center of volume. A surface of a boundary of a field of view that forms an angle of view of the imaging unit and the plane do not intersect outside the capsule endoscope.

6 Claims, 13 Drawing Sheets

U.S. PATENT DOCUMENTS

| | | | |
|---|---|---|---|
| 2006/0155174 A1* | 7/2006 | Glukhovsky et al. | 600/301 |
| 2006/0252986 A1 | 11/2006 | Akagi et al. | |
| 2007/0118017 A1* | 5/2007 | Honda | 600/160 |
| 2007/0118018 A1* | 5/2007 | Gilad et al. | 600/160 |
| 2008/0084478 A1* | 4/2008 | Gilad et al. | 348/207.99 |
| 2009/0105537 A1* | 4/2009 | Gat et al. | 600/109 |
| 2010/0010300 A1* | 1/2010 | Gilad | 600/109 |
| 2011/0034795 A9* | 2/2011 | Gilad et al. | 600/407 |

FOREIGN PATENT DOCUMENTS

| | | |
|---|---|---|
| JP | 2004-529718 | 9/2004 |
| JP | 2005-192820 | 7/2005 |
| WO | WO 02/095351 A2 | 11/2002 |
| WO | WO 2005/060348 A2 | 7/2005 |
| WO | WO 2005/062717 A2 | 7/2005 |

OTHER PUBLICATIONS

English language abstract of Japanese Patent Application No. JP 2003-325441 A dated Nov. 18, 2003 (full Japanese language copy previously submitted on May 26, 2009).

English language abstract of Japanese Patent Application No. JP 2005-192820 A dated Jul. 21, 2005 (full Japanese language copy previously submitted on May 26, 2009).

* cited by examiner

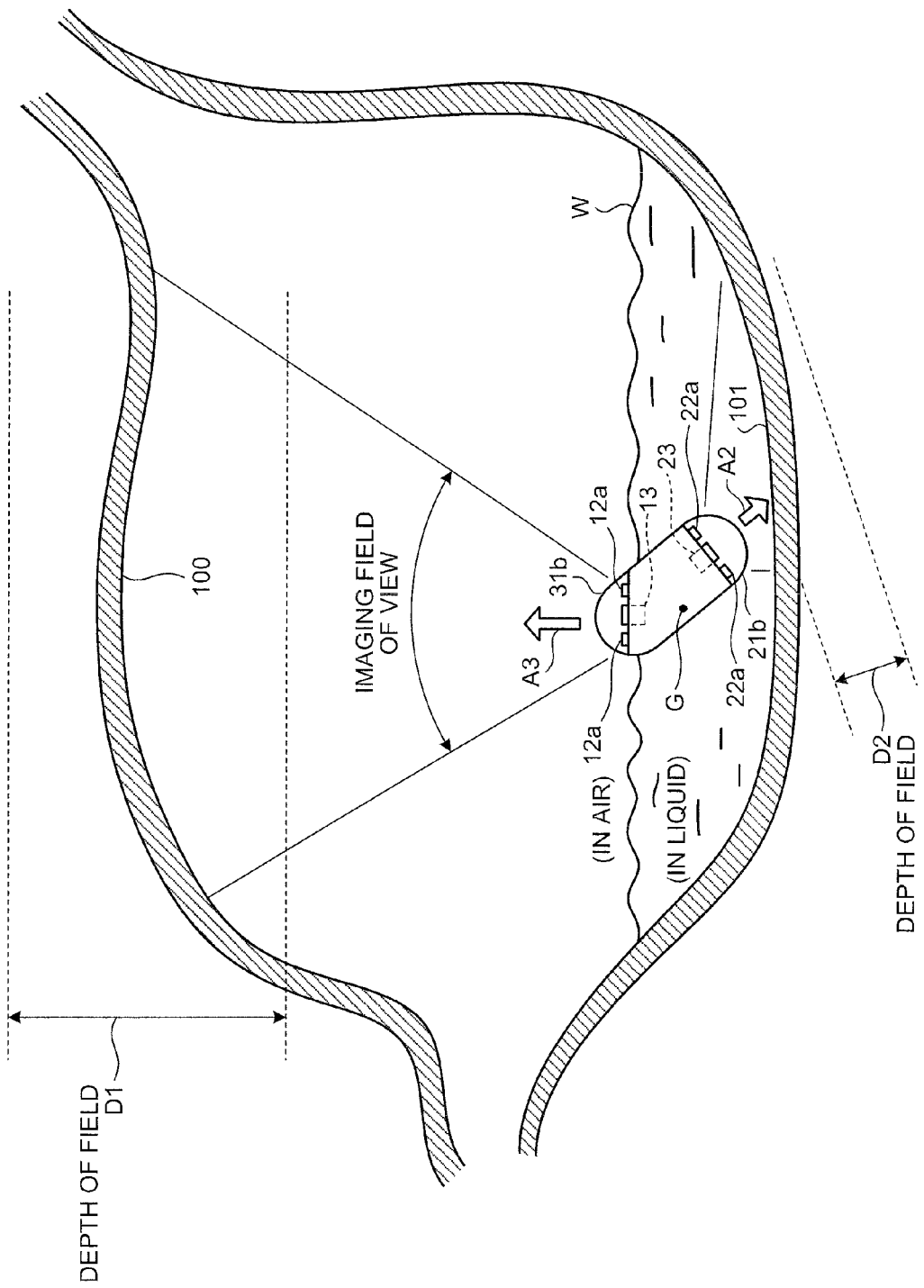

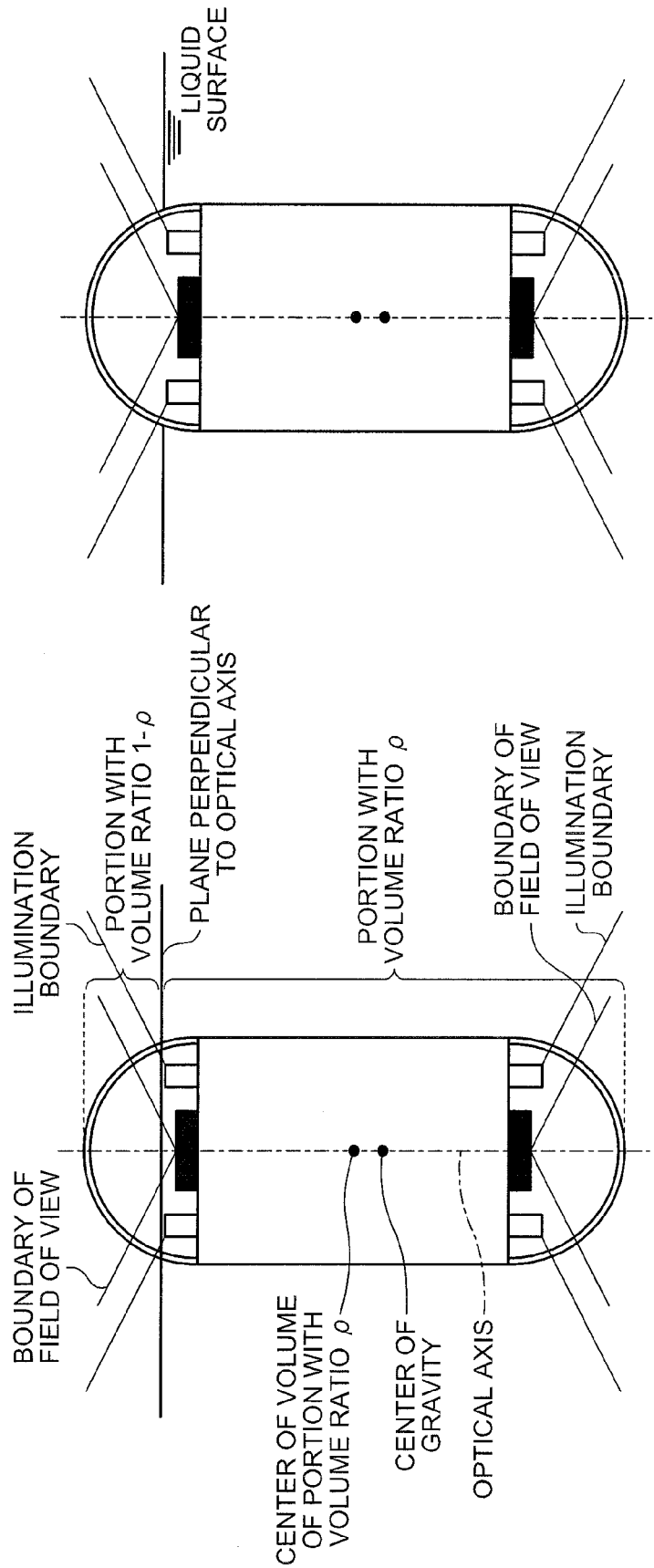

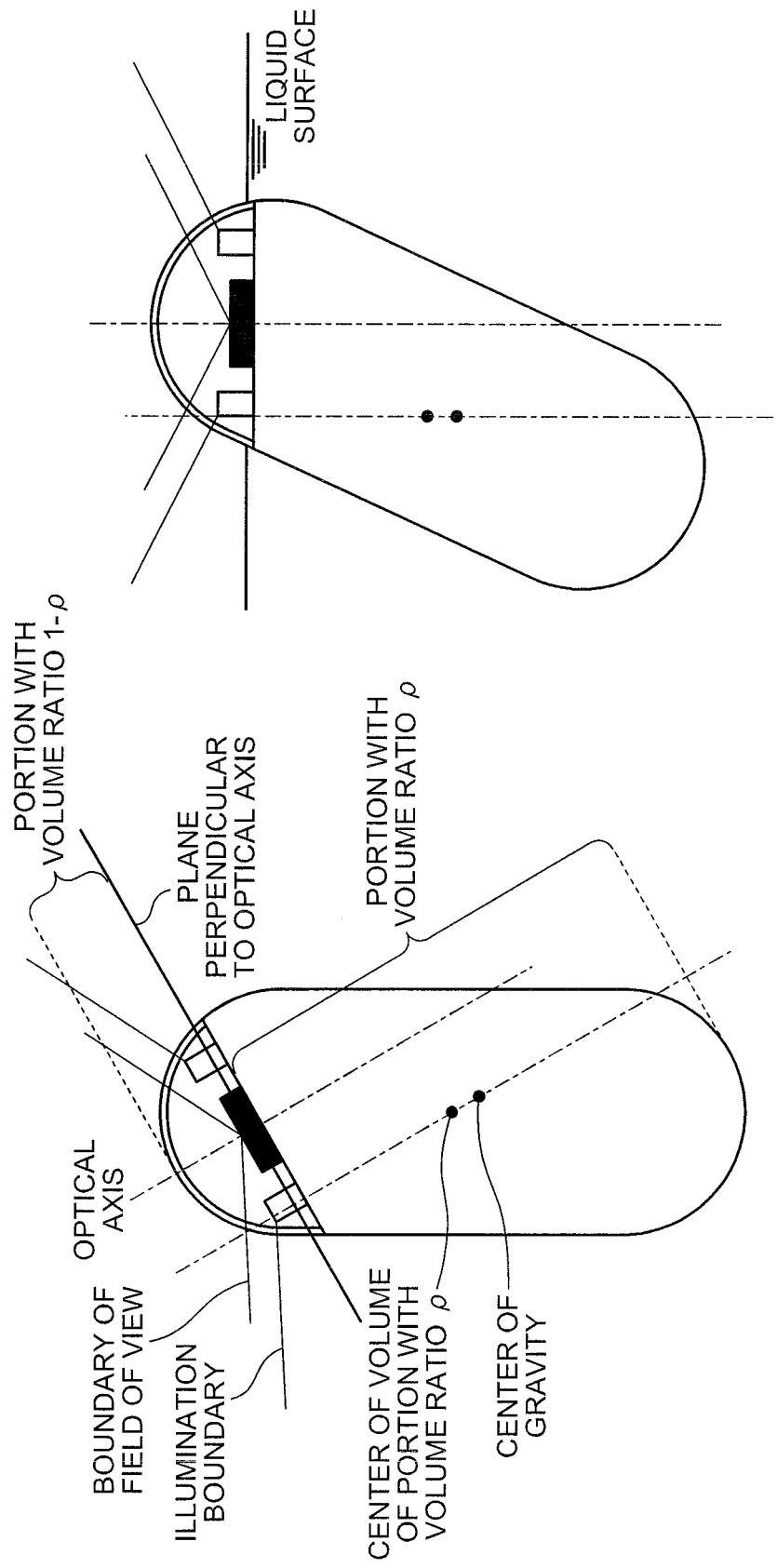

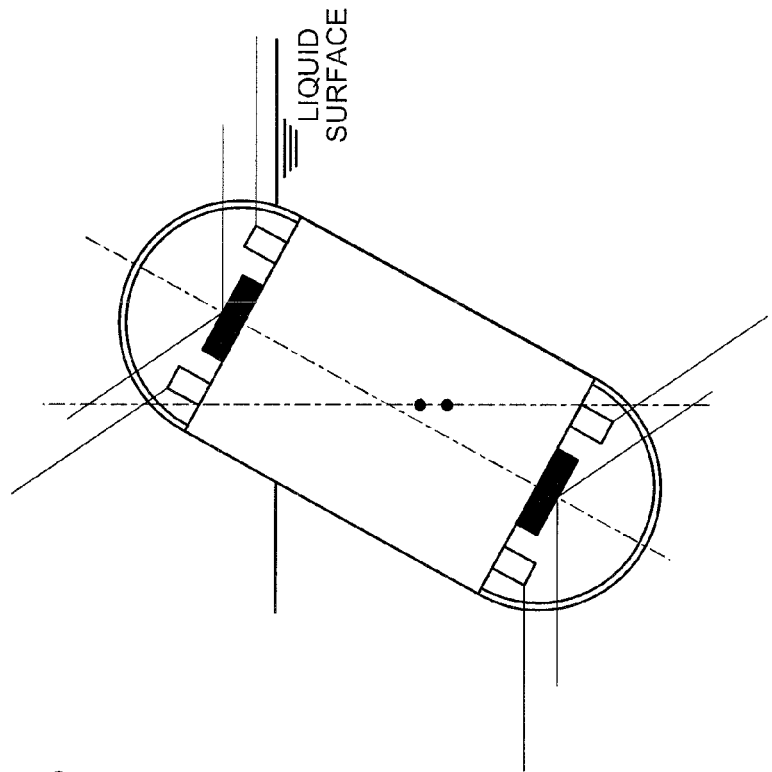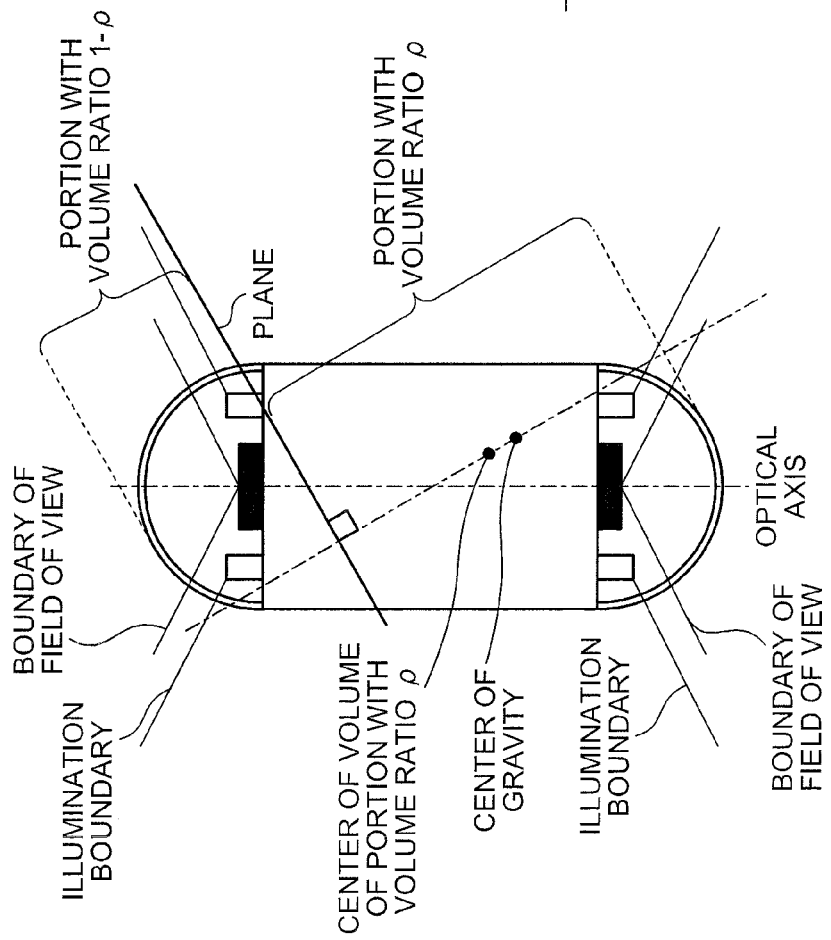

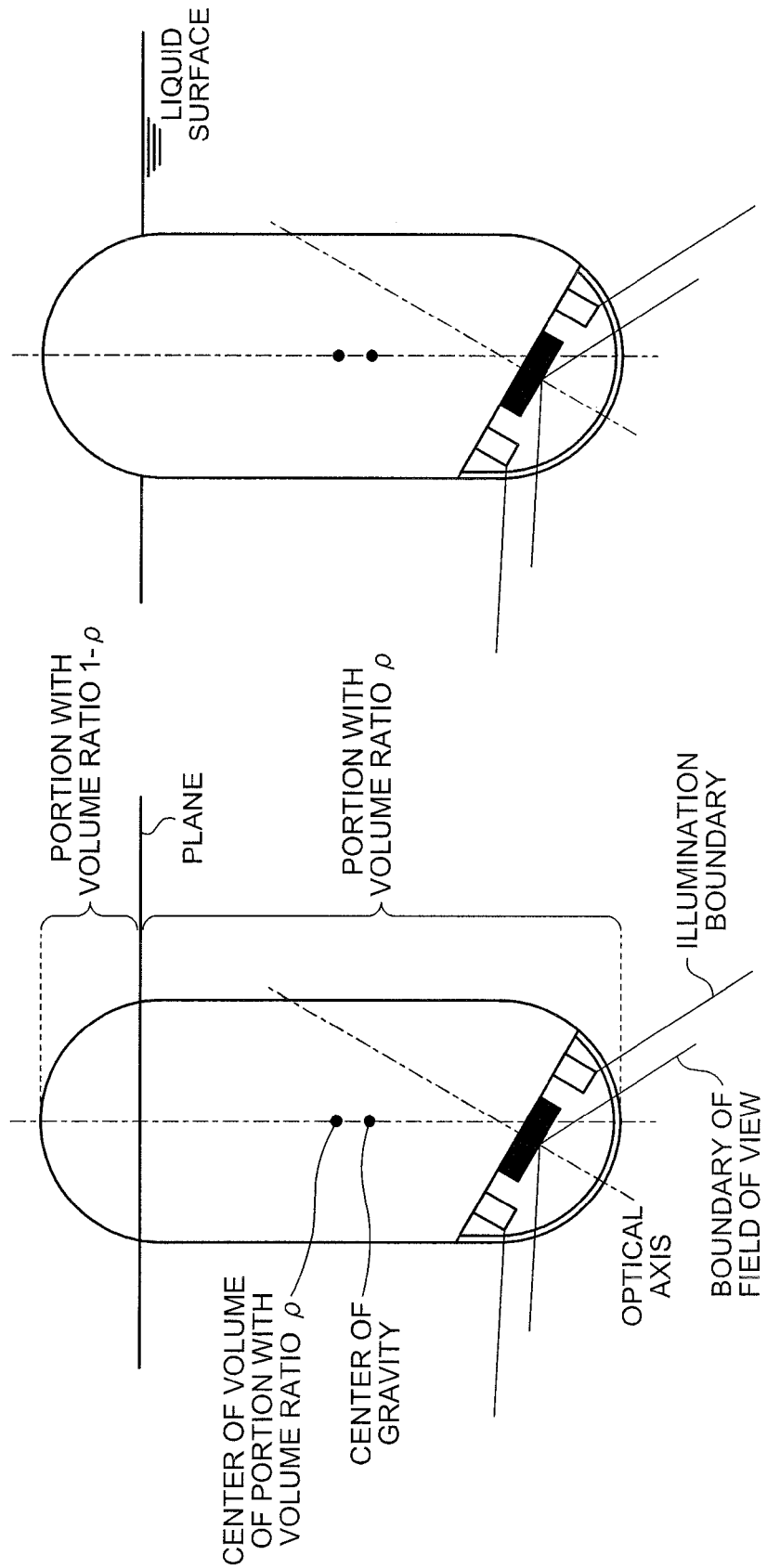

CAPSULE ENDOSCOPE

CROSS-REFERENCE TO RELATED APPLICATIONS

This application is a continuation of PCT international application Ser. No. PCT/JP2007/066799 filed on Aug. 29, 2007 which designates the United States, incorporated herein by reference, and which claims the benefit of priority from Japanese Patent Application No. 2006-317684, filed on Nov. 24, 2006, incorporated herein by reference.

BACKGROUND OF THE INVENTION

1. Field of the Invention

The present invention relates to a capsule endoscope that is introduced inside an organ of a subject such as a body of a patient, and that takes images of the inside of the organ.

2. Description of the Related Art

Conventionally, in a field of endoscope, a swallowable capsule endoscope that has an imaging function and a wireless communication function has been developed, and a system for obtaining internal body information of a subject with which in-vivo images of the subject using such a capsule endoscope has been proposed. After swallowed from the mouth of a subject for observation (examination), the capsule endoscope sequentially captures images of the inside of an organ in the subject (hereinafter, also referred to as "in-vivo images"), for example, at 0.5-second intervals, while traveling inside an organ such as stomach and small intestine by peristaltic movement until the capsule endoscope is naturally excreted outside.

While the capsule endoscope is traveling inside the subject, the in-vivo images are sequentially transmitted to a receiving apparatus placed outside the subject by wireless communication. The receiving apparatus includes a wireless communication function and a memory function, and sequentially stores images received from the capsule endoscope inside the subject in a recording medium. If the receiving apparatus is carried, the subject can freely act during the entire period from swallow until the capsule endoscope is naturally excreted.

After the capsule endoscope is excreted, a user such as a doctor and a nurse captures the images accumulated in the recording medium of the receiving apparatus in an image display device, and causes this image display device to display the images of an organ inside the subject on a display thereof. The user can make a diagnosis by checking the images inside the subject displayed on the image display device.

One of such capsule endoscopes is provided with a float to have a specific gravity of the entire apparatus of approximately 1, in other words, to float in water (for example, Published Japanese Translation No. 2004-529718 of PCT International Application). The capsule endoscope described in Published Japanese Translation No. 2004-529718 of PCT International Application floats in water that is introduced inside a digestive canal of a subject, and passes through the stomach, the small intestine, and the like in the subject in a short time by the effect of water flow and peristaltic movement of organs, to reach the large intestine. This capsule endoscope enables to take images inside the large intestine in the subject intensively.

SUMMARY OF THE INVENTION

According to an aspect of the present invention, a capsule endoscope includes a capsule-shaped casing and an imaging unit that is arranged inside the capsule-shaped casing in a fixed manner, and takes an image of an inside of an organ by the imaging unit in a state where the capsule endoscope is floating in liquid that is introduced inside the organ of a subject. Specific gravity of the capsule endoscope to the introduced liquid is $\rho$ ($\rho<1$), and a plane divides the capsule endoscope such that a volume ratio is to be $\rho:1-\rho$. A straight line that connects a center of volume of a portion whose volume ratio is $\rho$ and a center of gravity of the capsule endoscope is substantially perpendicular to the plane, and the center of gravity is present at a position farther distant from the plane than the center of volume. A surface of a boundary of a field of view that forms an angle of view of the imaging unit and the plane do not intersect with each other outside the capsule endoscope.

According to another aspect of the present invention, a capsule endoscope includes a capsule-shaped casing and an imaging unit that is arranged inside the capsule-shaped casing in a fixed manner, and takes an image of an inside of an organ by the imaging unit in a state where the capsule endoscope is floating in liquid that is introduced inside the organ of a subject. Specific gravity of the capsule endoscope to the introduced liquid is $\rho$ ($\rho<1$), and a plane divides the capsule endoscope such that a volume ratio is to be $\rho:1-\rho$. A straight line that connects a center of volume of a portion whose volume ratio is $\rho$ and a center of gravity of the capsule endoscope is substantially perpendicular to the plane, and the center of gravity is present at a position farther distant from the plane than the center of volume. The capsule endoscope includes an illuminating unit that illuminates an imaging field of view of the imaging unit. A surface of an illumination boundary that forms a distribution angle of illumination light that is emitted by the illuminating unit and the plane do not intersect with each other outside the capsule endoscope.

According to still another aspect of the present invention, a capsule endoscope includes a capsule-shaped casing and an imaging unit that is arranged inside the capsule-shaped casing in a fixed manner, and takes an image of an inside of an organ by the imaging unit in a state where the capsule endoscope is floating in liquid that is introduced inside the organ of a subject. Specific gravity of the capsule endoscope to the introduced liquid is $\rho$ ($\rho<1$), and a plane divides the capsule endoscope such that a volume ratio is to be $\rho:1-\rho$. A straight line that connects a center of volume of a portion whose volume ratio is $\rho$ and a center of gravity of the capsule endoscope is substantially perpendicular to the plane, and the center of gravity is present at a position farther distant from the plane than the center of volume. A distance from a point at which a surface of a boundary of a field of view that forms an angle of view of the imaging unit and the plane intersect with each other to the imaging unit is 3.2 times as long as a distance from a surface of the capsule endoscope to the imaging unit or longer.

According to still another aspect of the present invention, a capsule endoscope includes a capsule-shaped casing and an imaging unit that is arranged inside the capsule-shaped casing in a fixed manner, and takes an image of an inside of an organ by the imaging unit in a state where the capsule endoscope is floating in liquid that is introduced inside the organ of a subject. Specific gravity of the capsule endoscope to the introduced liquid is $\rho$ ($\rho<1$), and a plane divides the capsule endoscope such that a volume ratio is to be $\rho:1-\rho$. A straight line that connects a center of volume of a portion whose volume ratio is $\rho$ and a center of gravity of the capsule endoscope is substantially perpendicular to the plane, and the center of gravity is present at a position farther distant from the plane than the center of volume. The capsule endoscope includes an illuminating unit that illuminates an imaging field of view of the imaging unit. A distance from a point at which a surface of an illumination boundary that forms a distribution angle of illumination light that is emitted by the illuminating unit and the plane intersect with each other is 3.2 times as long as a distance from a surface of the capsule endoscope to the imaging unit or longer.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a schematic diagram for explaining operation of the capsule endoscope that images the inside of stomach alternately in air and in liquid in a state where the capsule endoscope is floating in an oblique position on the surface of the liquid inside the stomach of a subject;

FIGS. 8A and 8B are schematic diagrams showing a capsule endoscope whose optical axis of an imaging unit is perpendicular to the surface of liquid in a state where the capsule endoscope is floating in liquid introduced inside a body;

FIGS. 10A and 10B are schematic diagrams showing a modification of a capsule endoscope in which an optical axis of an imaging unit is perpendicular to the surface of liquid in a state where the capsule endoscope is floating in liquid introduced inside a body;

FIGS. 11A and 11B are schematic diagrams showing a capsule endoscope in which specific gravity, a position of the center of gravity, and a position of an imaging unit are set such that the water surface does not enter inside a boundary of a field of view and an illumination boundary in a state where the capsule endoscope is floating in liquid introduced inside a body;

FIGS. 12A and 12B are schematic diagrams showing a modification of the capsule endoscope in which specific gravity, a position of the center of gravity, and a position of an imaging unit are set such that the water surface does not enter inside a boundary of a field of view and an illumination boundary in a state where the capsule endoscope is floating in liquid introduced inside a body.

DETAILED DESCRIPTION OF THE PREFERRED EMBODIMENTS

Exemplary embodiments of a capsule endoscope according to the present invention are explained in detail below with reference to the accompanying drawings. The present invention is not limited to the embodiments.

Figure 1:
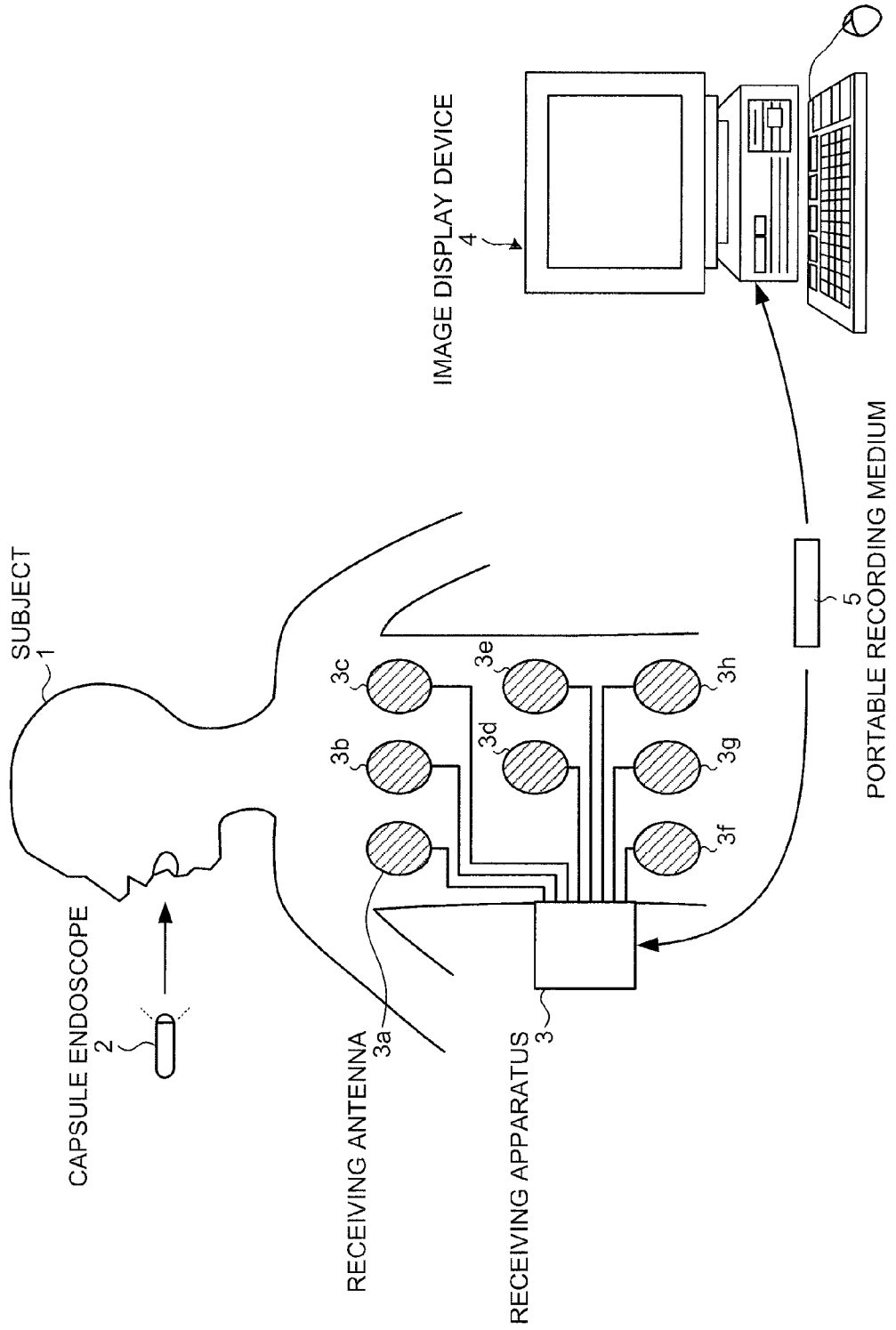
FIG. 1 is a schematic diagram showing a constitutional example of an in-vivo information acquiring system that has a capsule endoscope according to a first embodiment of the present invention.

FIG. 1 is a schematic diagram showing a constitutional example of an in-vivo information acquiring system that has a capsule endoscope according to a first embodiment of the present invention. As shown in FIG. 1, this in-vivo information acquiring system includes a capsule endoscope 2 that takes an image of the inside of a subject 1, a receiving apparatus 3 that receives the image of the inside of the subject 1 that is taken by the capsule endoscope 2, an image display device 4 that displays the image of the inside of the subject 1 received by the receiving apparatus 3, and a portable recording medium 5 used to communicate data between the receiving apparatus 3 and the image display device 4.

The capsule endoscope 2 has an imaging function of sequentially taking in-vivo images of the subject 1 chronologically, and a wireless communication function of sequentially transmitting the in-vivo images of the subject 1 outside by wireless communication. The specific gravity of the capsule endoscope 2 is set such that the capsule endoscope 2 floats on the surface of desirable liquid such as water. The capsule endoscope 2 thus configured is introduced inside an organ of the subject 1, and takes images of the inside of the organ. When a predetermined amount of liquid such as water is introduced inside this organ, the capsule endoscope 2 floats on the surface of the liquid introduced inside this organ, takes a specific floating posture, and sequentially takes images in a wide range inside the organ in the specific posture. The images of the inside of the organ taken by the capsule endoscope 2 are sequentially transmitted to the receiving apparatus 3 outside the subject 1 by wireless communication. When the capsule endoscope 2 is introduced inside an organ of the subject 1, the capsule endoscope 2 travels along a digestive canal of the subject 1 by peristaltic movement of organs or the like. At the same time, the capsule endoscope 2 sequentially takes in-vivo images of the subject 1 at predetermined intervals, for example, at 0.5-second intervals, and sequentially transmits the obtained in-vivo images of the subject 1 to the receiving apparatus 3.

To the receiving apparatus 3, a plurality of receiving antennas 3a to 3h that are arranged in a dispersed manner on a surface of the subject 1, for example, are connected, and receives a radio signal from the capsule endoscope 2 through the receiving antennas 3a to 3h to obtain the in-vivo images of the subject 1 included in the received radio signal. Furthermore, to the receiving apparatus 3, the portable recording medium 5 is detachably inserted, and sequentially stores the in-vivo images of the subject 1 in the portable recording medium 5.

The receiving antennas 3a to 3h are implemented by, for example, a loop antenna, and receive a radio signal that is transmitted by the capsule endoscope 2. Such receiving antennas 3a to 3h are arranged in a dispersed manner at predetermined positions, for example, positions corresponding to a traveling route (that is, a digestive canal) of the capsule endoscope 2 inside the subject 1, on the body surface of the subject 1. The receiving antennas 3a to 3h can be arranged at predetermined positions on a jacket to be worn on the subject 1 in a dispersed manner. In this case, when this jacket is put on the subject 1, the receiving antennas 3a to 3h are arranged at the predetermined positions on the body surface of the subject 1 corresponding to the traveling route of the capsule endoscope 2 inside the subject 1. Such receiving antennas 3a to 3h are only required to be arranged at least one for the subject 1, and the number of antennas to be arranged is not limited to eight.

The portable recording medium 5 is a recording medium that can be carried, such as CompactFlash (registered trademark). The portable recording medium 5 is detachably attached to the receiving apparatus 3 and the image display device 4, and has a configuration that enables output and record of data when attached to the respective apparatuses. Specifically, the portable recording medium 5 sequentially stores various kinds of data such as a group of in-vivo images of the subject 1 obtained by the receiving apparatus 3 when attached to the receiving apparatus 3. On the other hand, the portable recording medium 5 outputs the stored data such as a group of in-vivo images of the subject 1 to the image display device 4 when attached to the image display device 4. Thus, the data stored in the portable recording medium 5 is captured on the image display device 4. In addition, patient information on the subject 1 such as patient name and patient ID is written in the portable recording medium 5 by the image display device 4.

The image display device 4 is to display the in-vivo images of the subject 1 taken by the capsule endoscope 2 and the like. Specifically, the image display device 4 has a configuration such as that of a workstation that captures various kinds of data such as a group of the in-vivo images of the subject 1 through the portable recording medium 5 described above, and that displays the group of the in-vivo images of the subject 1 on a display. The image display device 4 thus configured has a processing function for a user such as a doctor and a nurse to observe (examine) the in-vivo images of the subject 1 to make a diagnosis. In this case, the user causes the image display device 4 to sequentially display the in-vivo images of the subject 1 to observe (examine) a part inside the subject 1 such as esophagus, stomach, small intestine, and large intestine, and makes a diagnosis based on this observation.

Figure 2:
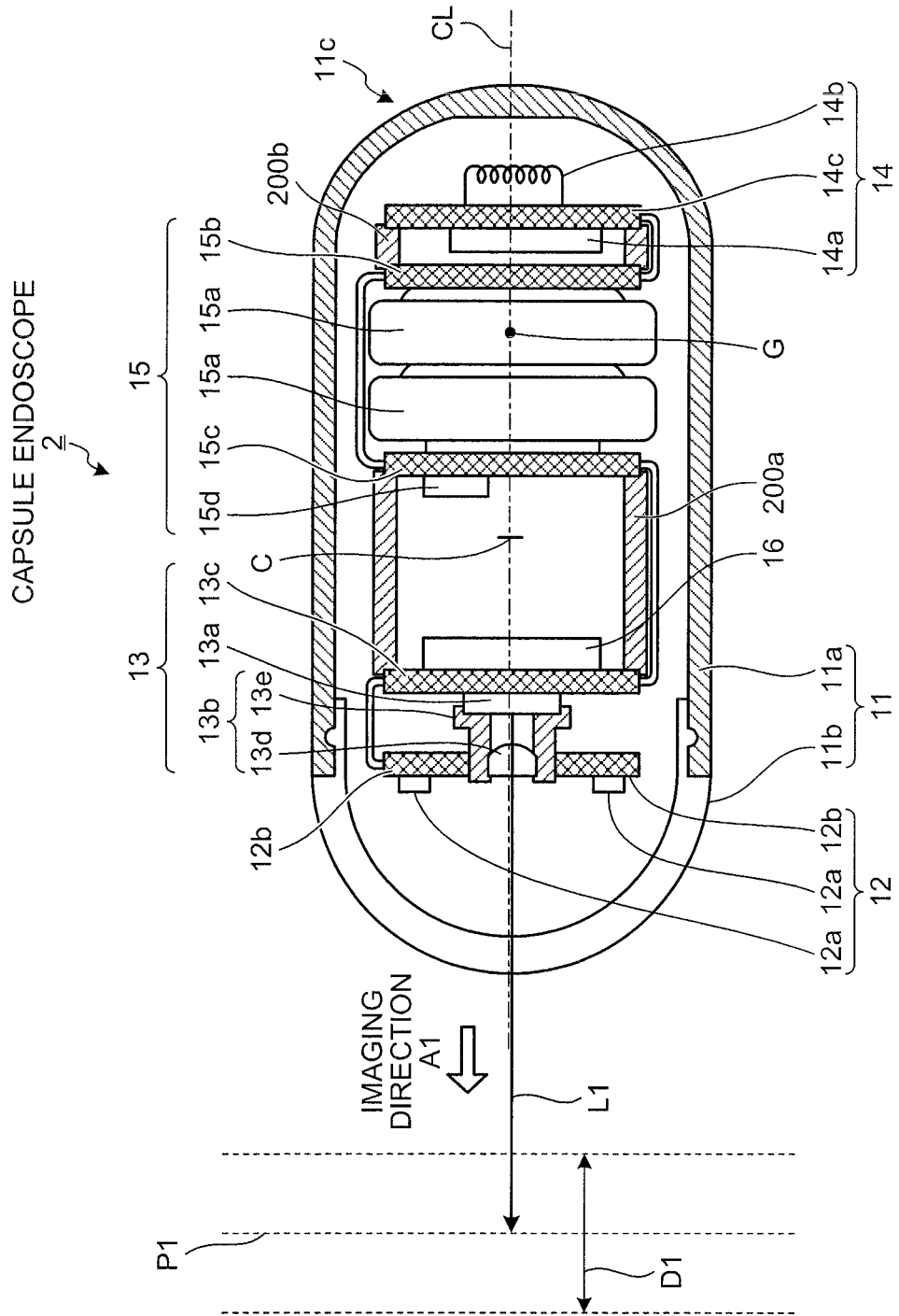
FIG. 2 is a schematic side cross-section showing a constitutional example of the capsule endoscope according to the first embodiment of the present invention.

Next, a configuration of the capsule endoscope 2 according to the first embodiment of the present invention is explained. FIG. 2 is a schematic side cross-section showing a constitutional example of the capsule endoscope 2 according to the first embodiment of the present invention. As shown in FIG. 2, the capsule endoscope 2 according to the first embodiment includes a casing 11 formed in a capsule form, an illuminating unit 12 that illuminates inside an organ of a subject, an imaging unit 13 that takes images (in-vivo image of a subject) of the inside of an organ of the subject illuminated by the illuminating unit 12, and a wireless communication unit 14 that transmits the in-vivo images of the subject taken by the imaging unit 13 outside by wireless communication. Furthermore, the capsule endoscope has a power source unit 15 that supplies driving power to respective components and a control unit 16 that controls the respective components.

The casing 11 is a capsule-shaped casing that is formed in a size easy to be introduced inside the subject, and is formed with a casing main body 11a and an optical dome 11b. The casing main body 11a is a tubular casing in which one end is open and the other end (that is, a dome portion 11c) is closed in a dome shape, and houses therein the respective components of the capsule endoscope 2, such as the illuminating unit 12, the imaging unit 13, the wireless communication unit 14, the power source unit 15, and the control unit 16.

The optical dome 11b is a transparent dome-shaped optical member, and is attached at an opening end being one end of the casing main body 11a, and closes this opening end. On an outer surface of the optical dome 11b, a transparent water-drop protective film is formed. The transparent water-drop protective film formed on the outer surface of the optical dome 11b can be a water-repellent film or a hydrophilic film.

The casing 11 formed with the casing main body 11a and the optical dome 11b houses the respective components (the illuminating unit 12, the imaging unit 13, the wireless communication unit 14, the power source unit 15, the control unit 16, etc.) of the capsule endoscope 2 in a fluid-tight manner.

The illuminating unit 12 functions as an illuminating means to illuminate the inside (that is, an object of the imaging unit 13) of an organ of the subject to be imaged by the imaging unit 13. Specifically, the illuminating unit 12 is arranged on a side of the optical dome 11b in the casing 11, and illuminates an object of the imaging unit 13 through the optical dome 11b. This illuminating unit 12 has a plurality of light emitting devices 12a that emit illumination light to an object of the imaging unit 13, and an illumination board 12b on which a circuit to implement the function of the illuminating unit 12 is formed.

The light emitting devices 12a are mounted on the illumination board 12b, and emit illumination light to an imaging field of view of the imaging unit 13 through the optical dome 11b. The light emitting devices 12a illuminate an object of the imaging unit 13 (that is, the inside of an organ of the subject) with the illumination light. These light emitting devices 12a emit illumination light of large emitting amount compared to an illuminating unit of a conventional capsule endoscope (capsule endoscope that images the inside of an organ of a subject from a short distance), depending on an object of the imaging unit 13. The illumination board 12b is, for example, a rigid circuit board that is formed in a disc shape, and is arranged on a side of the optical dome 11b in the casing 11. In a central part of the illumination board 12b, a lens frame of the imaging unit 13 described later is inserted.

The imaging unit 13 functions as an imaging means that takes an image of an object (inside of an organ of the subject) illuminated by the illuminating unit 12. Specifically, the imaging unit 13 is fixed on a side of the optical dome 11b inside the casing 11, and takes an image of an object in an imaging direction A1 that is determined by posture (in detail, floating posture of the casing 11 that floats on the surface of liquid) of the casing 11. The imaging unit 13 has a solid-state imaging device 13a such as CCD and CMOS, an optical system 13b that images the image of an object on a light receiving surface of the sold-state imaging device 13a, and an imaging board 13c on which a circuit that implements the function of the imaging unit 13 is formed.

The solid-state imaging device 13a captures an image of an object that is illuminated by the illuminating unit 12. Specifically, the solid-state imaging device 13a has an imaging field of view in the imaging direction A1 determined by the floating posture of the casing 11, and captures an image of the inside of an organ (that is, an object) inside the imaging field of view illuminated by the illuminating unit 12. Further specifically, the solid-state imaging device 13a has a light receiving surface that receives light from an object that is positioned in the imaging field of view, and performs photoelectric conversion on light from the object received on through this light receiving surface to capture an image of the object (that is, an in-vivo image). Optical characteristics such as a light receiving amount of the solid-state imaging device 13a are set depending on the object in the imaging direction A1.

The optical system 13b has a lens 13d that images an image of an object on the light receiving surface of the solid-state imaging device 13a, and a lens frame 13e that holds this lens 13d. The lens 13d collects light from the object present in the imaging direction A1 on the light receiving surface of the solid-state imaging device 13a, and images the image of the object on the light receiving surface of the solid-state imaging device 13a. Optical characteristics such as focal length and depth of field of the lens 13d are set depending on an object in the imaging direction A1.

The lens frame 13e has a tubular structure in which both ends are open, and holds the lens 13d inside a tubular portion thereof. Specifically, the lens frame 13e holds the lens 13d inside the tubular portion near an opening at one end. Moreover, the other end of the lens frame 13e is fixed to the solid-state imaging device 13a in so as to guide light from an object onto the light receiving surface of the solid-state imaging device 13a. The lens frame 13e holds the lens 13d at a position in a predetermined distance from the solid-state imaging device 13a described above. Distance between the solid-state imaging device 13a and the lens 13d that is defined by the lens frame 13e is set depending on an object in the imaging direction A1. The one end of the lens frame 13e (on a side on which the lens 13d is held) is inserted to the illumination board 12b described above, and is fixed to the illumination board 12b.

The imaging board 13c is, for example, a rigid circuit board that is formed in a disc shape, and is arranged on a side of the optical dome 11b in the casing 11 in a fixed manner. Specifically, the imaging board 13c is fixed at a position on a side of the dome portion 11c in the casing main body 11a relative to illumination board 12b. On the imaging board 13c, the solid-state imaging device 13a and the control unit 16 described above are mounted.

The wireless communication unit 14 functions as a wireless communication means that sequentially transmits an in-vivo image that is imaged by the imaging unit 13 to the receiving apparatus 3 (see FIG. 1) outside by wireless communication. Specifically, the wireless communication unit 14 is arranged on a side of the dome portion 11c in the casing 11 in a fixed manner, and sequentially transmits an image of the inside of an organ being the object in the imaging direction A1 to the receiving apparatus 3 by wireless communication. The wireless communication unit 14 has a wireless unit 14a that generates a radio signal including an in-vivo image of the subject, an antenna 14b that sends the radio signal generated by the wireless unit 14a to the outside, and a wireless board 14c on which a circuit that implements the function of the wireless unit 14 is formed.

The wireless unit 14a receives an image signal including an in-vivo image of the subject imaged by the solid-state imaging device 13a described above, and performs modulation processing and the like on the received image signal. The wireless unit 14a generates a radio signal that includes the in-vivo image of the subject. The antenna 14b is a loop or coil antenna, and sequentially sends the radio signal generated by the wireless unit 14a to the receiving apparatus 3 present outside the subject. The wireless board 14c is, for example, a rigid circuit board that is formed in a disc shape, and is arranged on a side of the dome portion 11c in the casing 11, for example. On the wireless board 14c, the wireless unit 14a and the antenna 14b are mounted.

The power source unit 15 is arranged on a side of the dome portion 11c in the casing 11, and supplies driving power to the respective components (namely, the illuminating unit 12, the imaging unit 13, the wireless communication unit 14, the control unit 16, etc.) of the capsule endoscope 2 according to the first embodiment. The power source unit 15 has a battery 15a having predetermined power, power source boards 15b and 15c on which a circuit that implements the function of the power source unit 15 is formed, and a switch 15d that switches on and off for power supply from the battery 15a.

The battery 15a is, for example, a button battery such as a silver oxide cell, and is connected between the power source boards 15b and 15c as shown in FIG. 2 in the required number of pieces (for example, two pieces). The power source boards 15b and 15c have a positive terminal and a negative terminal that are electrically connected to the battery 15a. The power source board 15b, 15c and the circuit boards (namely, the illumination board 12b, the imaging board 13c, and the wireless board 14c) of the respective components of the capsule endoscope 2 are electrically connected by a flexible substrate or the like. The switch 15d is, for example, a reed switch that switches on and off by application of a magnetic force from an external source, and is provided on the power source board 15c. Specifically, the switch 15d controls supply of power to the respective components of the capsule endoscope 2 from the battery 15a.

The control unit 16 is mounted, for example, on the imaging board 13c, and controls the respective components of the capsule endoscope 2 according to the first embodiment. Specifically, the control unit 16 controls the light emitting devices 12a of the illuminating unit 12, the solid-state imaging device 13a of the imaging unit 13, and the wireless unit 14a of the wireless communication unit 14. Further specifically, the control unit 16 controls operation timing of the light emitting devices 12a and the solid-state imaging device 13a so that the solid-state imaging device 13a captures an image of the object at predetermined time intervals in synchronization with the light emitting operation of the light emitting devices 12a. The control unit 16 has various kinds of parameters related to an image processing such as white balance, and has an image processing function of generating an image signal that includes an image of the object (in-vivo image of the subject) captured by the solid-state imaging device 13a. Moreover, the control unit 16 transmits the image signal including an in-vivo image of the subject to the wireless communication unit 14, and controls the wireless unit 14a to generate and output a radio signal including the in-vivo image of the subject.

Next, the specific gravity and the center of gravity of the capsule endoscope 2 according to the first embodiment are explained. The capsule endoscope 2 has such a configuration that the illuminating unit 12, the imaging unit 13, the wireless communication unit 14, the power source unit 15, and the control unit 16 are housed in the casing 11 in a capsule form, as described above (see FIG. 2). The capsule endoscope 2 having such a configuration floats on the surface of liquid that is introduced inside an organ of the subject. In other words, the specific gravity of the capsule endoscope 2 is set to be lower than the specific gravity of a predetermined liquid (for example, water) that is introduced inside an organ of the subject.

Specifically, the specific gravity of the capsule endoscope 2 that floats on the surface of liquid is obtained, for example, by forming empty space equal to or larger than a predetermined volume inside the casing 11 or by providing a float member (not shown) to the casing 11. If the liquid introduced inside an organ of the subject is water, for example, the capsule endoscope 2 is arranged to have the specific gravity equal to or lower than the specific gravity of water (=1). It is preferable that the capsule endoscope 2 have the specific gravity with which one half (for example, the optical dome 11b) of the capsule endoscope 2 floating on the surface of the liquid introduced inside an organ of the subject is out of this liquid.

On the other hand, the center of gravity of the capsule endoscope 2 is set so that the floating posture of the capsule endoscope 2 in a state where the capsule endoscope is floating on the surface of liquid, that is the floating posture of the casing 11 is maintained in a specific posture. Specifically, as shown in FIG. 2, a center of gravity G of the capsule endoscope 2 is set at a position deviated from a center C of the casing 11 by arranging the battery 15a of the power source unit 15 on a side of the dome portion 11c inside the casing 11 relative to the center C of the casing 11, for example. In this case, the center of gravity G is set on the opposite side to the imaging unit 13 described above relative to the center C of the casing 11. In other words, the imaging unit 13 is fixed at a position inside the casing 11 on the opposite side to the center of gravity G relative to the center C of the casing 11.

To set the specific gravity and the center of gravity of the capsule endoscope 2 as described above, it is required to appropriately arrange the respective components in the capsule endoscope 2. However, an appropriate arrangement of the respective components cannot be maintained just by folding a circuit board electrically connected through a flexible substrate. For this reason, a spacer is provided between the components so that the appropriate arrangement of the respective components is maintained easily. Specifically, as shown in FIG. 2, a spacer 200a is arranged between the imaging board 13c and the power source board 15c, and a spacer 200b is arranged between the power source board 15c and the wireless board 14c so that intervals are appropriately kept between circuit boards. As a result, the appropriate arrangement of the respective components required to set the specific gravity and the center of gravity of the capsule endoscope 2 is achieved with ease. By using MID (molded interconnect device) as the spacer, the spacer can serve as both the flexible substrate and the spacer.

By thus setting the center of gravity G of the capsule endoscope 2 at a position deviated from the center C of the casing 11, the floating posture of the casing 11 in a state where the capsule endoscope 2 is floating on the surface of liquid can be maintained to a specific floating posture. Specifically, the floating posture of the casing 11 is maintained in such a specific floating posture that the imaging direction A1 of the imaging unit 13 is directed upward of the liquid (liquid in which the capsule endoscope 2 floats).

The imaging unit 13 described above is arranged such that the optical axis (that is, optical axis of the lens 13d) of the imaging unit 13 corresponding to the imaging direction A1 is parallel to or on the same straight line as a center axis CL in the longitudinal direction of the casing 11 in a fixed manner. In this case, the center of gravity G of the capsule endoscope 2 is set at a position deviated from the center C of the casing 11 and on or near the center axis CL. By arranging the center of gravity G at such a position, the floating posture of the casing 11 is maintained in the specific posture in which the imaging direction A1 of the imaging unit 13 is directed substantially vertically upward.

A subject in the imaging direction A1 determined by the floating posture of the casing 11 is an object in air that is positioned above the liquid in which the capsule endoscope 2 floats. In this case, the imaging unit 13 described above captures an image of the object in air present in the imaging direction A1 through the optical dome 11b.

Next, optical characteristics of the imaging unit 13 that images an object in the imaging direction A1 determined by the floating posture of the casing 11 are explained. The imaging unit 13 images an object present in the imaging direction A1 determined by the floating posture of the casing 11 when the capsule endoscope 2 floats on the surface of liquid introduced inside an organ of the subject as described above. In this case, the imaging unit 13 images the object in air present in the imaging direction A1 through the optical dome 11b. The optical characteristics of the imaging unit 13 are set depending on an object (object in air) in the imaging direction A1 that is determined by the floating posture of the casing 11. The optical characteristics of the imaging unit 13 include an image forming property that determines a position of a focal point in the imaging direction A1, depth of field at the focal point in the imaging direction A1, an angle of view that defines the imaging field of view of the imaging unit 13, a light receiving amount when an image of the object is imaged, and the like.

The imaging forming property of the imaging unit 13 is an optical characteristic to determine the focal point of the imaging direction A1, and is set, for example, by adjusting a distance between the solid-state imaging device 13a and the lens 13d, and the focal length of the lens 13d. As the image forming property of the imaging unit 13, the focal point is set at a point P1 that is distant from the imaging unit 13 by a distance L1 in the imaging direction A1, as shown in FIG. 2. The distance L1 in the imaging direction A1 is substantially equal to a distance from an object in air that is present above the liquid introduced inside an organ of the subject to the capsule endoscope 2 (specifically, the imaging unit 13) that is floating in the liquid inside the organ. By thus setting the focal point at a position P1 in the imaging direction A1, the imaging unit 13 of the capsule endoscope 2 in a floating state on the surface of the liquid inside the organ can focus at a position near the object in air present above the liquid (specifically, near an inner wall of the organ in air).

The distance L1 in the imaging direction A1 is longer than a distance between the imaging unit of the conventional capsule endoscope that images the inside of an organ whose inner space is small such as esophagus and small intestine from a short distance and an object. Therefore, as the image forming property of the imaging unit 13, the focal point is set at the point P1 that is farther than the focal point of the conventional capsule endoscope.

Depth of field D1 of the imaging unit 13 is set by adjusting the distance between the solid-state imaging device 13a and the lens 13d, the focal length of the lens 13d, the distance L1 in the imaging direction A1, and the like. The depth of field D1 thus set is set to have a predetermined range from the point P1 in the imaging direction A1 as the center as shown in FIG. 2. Specifically, the depth of field D1 is set such that the object in air that is present in the imaging direction A1 is positioned inside a region between a near point and a far point of the imaging unit 13, considering the position of the surface of liquid inside an organ of the subject and a stretching action of the organ.

The angle of view of the imaging unit 13 defines the imaging field of view of the imaging unit 13, and is set, for example, by adjusting the distance between the solid-state imaging device 13a and the lens 13d, the focal length of the lens 13d, the light receiving surface of the solid-state imaging device 13a, and the like. The angle of view of the imaging unit 13 is set so as to take an object in a wider range inside the imaging field of view than that of the conventional capsule endoscope that images the inside of an organ whose inner space is small such as esophagus and small intestine from a short distance. In this case, it is preferable that the angle of view of the imaging unit 13 be set to wide angle compared to the conventional capsule endoscope that is suitable for imaging from a short distance.

The light receiving amount of the imaging unit 13 when an image of an object is captured is set to be greater than that of the imaging unit of the conventional capsule endoscope that is suitable for imaging of the inside of an organ whose inner space is small such as esophagus and small intestine from a short distance. Specifically, the light emitting devices 12a of the illuminating unit 12 described above emits illumination light in a light emitting amount sufficient to illuminate an object in air present in the imaging direction A1 (greater light emitting amount compared to the conventional capsule endoscope suitable for imaging from a short distance). As the light receiving amount of the imaging unit 13 (specifically, the solid-state imaging device 13a), light receiving sensitivity thereof is set suitably for receiving reflection light from the object in air that occurs when the illumination light of the light emitting devices 12a is irradiated on the object in air. Thus, the light receiving amount of the imaging unit 13 is to be sufficient to take a clear image of the object in air in a wide range.

Figure 3:
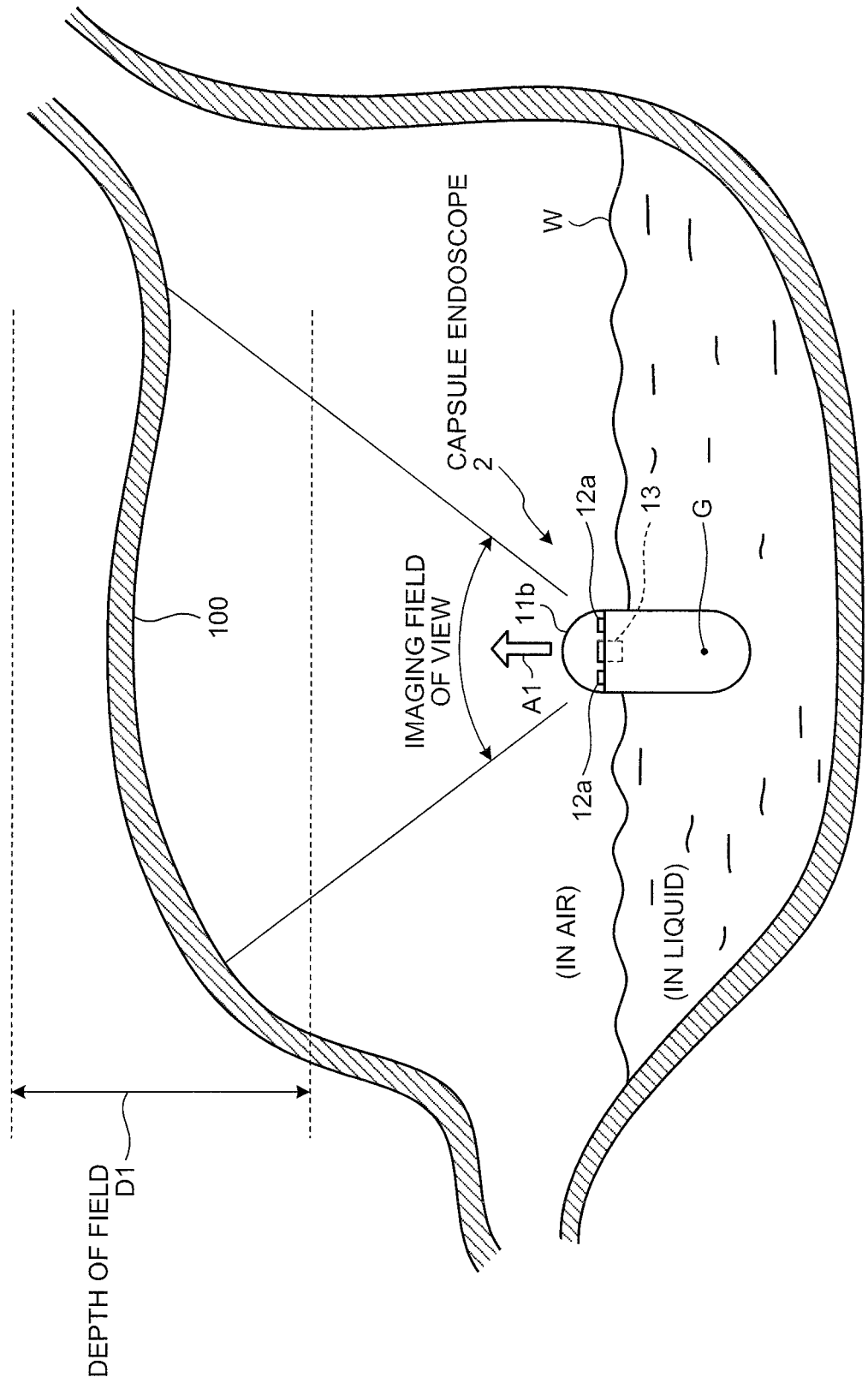
FIG. 3 is a schematic diagram for explaining operation of the capsule endoscope that images the inside of stomach in air, in a floating state on the surface of water inside the stomach of a subject.

Next, operation of the capsule endoscope 2 that takes an image of the inside of the stomach of the subject 1 in a state where the capsule endoscope 2 is floating in water when the capsule endoscope 2 and a required amount of water are introduced inside the stomach of the subject 1 as one example of organs whose inner space is large is explained. FIG. 3 is a schematic diagram for explaining operation of the capsule endoscope 2 that images the inside of stomach in air, in a floating state on the surface of water inside the stomach of the subject 1.

First, the capsule endoscope 2 is taken in through the mouth of the subject 1 with a required amount of water, to be introduced inside the stomach of the subject 1. In this case, because the capsule endoscope 2 is set to have the specific gravity equal to or lower than the specific gravity of water (for example, about 0.8), the capsule endoscope 2 floats on the surface of the water inside the stomach of the subject 1. Thereafter, the capsule endoscope 2 in a floating state on the surface of the water takes images of the inside of the stomach of the subject 1 with the imaging unit 13 maintaining the specific floating posture.

Specifically, as shown in FIG. 3, the capsule endoscope 2 set to have the specific gravity equal to or lower than that of water floats on the surface of a required amount of water W that is introduced inside the stomach of the subject 1 and takes the specific floating posture. The center of gravity G of the capsule endoscope 2 is set at a position deviated from the center C of the casing 11 and opposite to the imaging unit 13 relative to the center C (preferably, on the center axis CL) as described above. When the center of gravity G is set at such a position, the capsule endoscope 2 in a floating state takes the specific floating posture at the surface of the water W, that is, the floating posture in which the optical dome 11b is out of the water surface. In this case, the casing 11 maintains such a floating posture that the casing main body 11a on a side of the dome portion 11c is submerged under the surface of the water W (in liquid) and the imaging direction A1 of the imaging unit 13 is directed upward from the water W by the center of gravity G.

By such a floating posture of the casing 11, the imaging direction A1 of the imaging unit 13 is determined to be upward from the water W (for example, vertically upward). The imaging unit 13 takes an image of an object in air that is positioned in the imaging direction A1 determined by the floating posture of the casing 11. Specifically, the light emitting devices 12a sufficiently illuminate an inside of stomach 100 in air being the object in the imaging direction A1. The imaging unit 13 captures an image of the inside of stomach 100 that is sufficiently illuminated by the light emitting devices 12a.

The optical characteristics of the imaging unit 13 are set depending on an object (namely, the inside of stomach 100 in air) in the imaging direction A1 that is determined by the floating posture of the casing 11. Specifically, as the image forming property of the imaging unit 13, the focal point is set near the object in air present in the imaging direction A1, that is, near a wall of the inside of stomach 100 in air. In this case, the distance between the solid-state imaging device 13a and the lens 13d, the focal length of the lens 13d, and the like are adjusted so that the distance L1 in the imaging direction A1 is substantially equal to a distance (subject distance) from the imaging unit 13 of the capsule endoscope 2 that is floating in on the surface of the water W to the inside of stomach 100 in air.

The depth of field D1 of the imaging unit 13 is set such that the inside of stomach 100 in air is positioned inside a region between a near point and a far point of the imaging unit 13 in the imaging direction A1 (that is, a focus area of the imaging unit 13). The angle of view of the imaging unit 13 is set so as to take the inside of stomach 100 in air that is present inside the focus range of the imaging unit 13 in a wide range (that is, a wide range compared to the case where the inside of stomach is imaged from a short distance). The light receiving amount of the imaging unit 13 is set to a light receiving sensitivity suitable for receiving reflection light from the inside of stomach 100 in air that is generated when the inside of stomach 100 in air is irradiated with the illumination light of the light emitting devices 12a described above.

The imaging unit 13 whose optical characteristics are set depending on an object (the inside of stomach 100 in air) in the imaging direction A1 as described above has a focus area at a farther point than that in the case where the inside of an organ is imaged from a short distance, and takes the inside of stomach 100 in air that is positioned inside the focus area at the far point in the imaging field of view that is determined by the angle of view. Furthermore, the inside of stomach 100 in air taken in the imaging field of view of the imaging unit 13 is sufficiently illuminated by the light emitting devices 12a. If water drops are generated on the outer surface of the optical dome 11b, the image captured by the imaging unit through the optical dome 11b can be unclear; however, because the transparent water-drop protective film such as a water-repellent film and a hydrophilic film is formed on the outer surface of the optical dome 11b, it is possible to prevent water drops on the outer surface of the optical dome 11b. For example, if a water-repellent film of silicon base, fluorine base, or the like is formed on the outer surface of the optical dome 11b, even if a water drop adheres on the optical dome 11b, it is possible to avoid the water drop staying on the outer surface of the optical dome 11b and to let the water drop run down. Therefore, the imaging through the optical dome 11b is not disturbed by water drops. On the other hand, if a hydrophilic transparent film is formed on the outer surface of the optical dome 11b, even if a water drop adheres on the optical dome 11b, this water drop becomes a film uniform with the outer surface of the optical dome 11b. Therefore, the imaging through the optical dome 11b is not disturbed by water drops. Accordingly, the imaging unit 13 can capture a clear and wide range image of the inside of stomach 100 in air present in the imaging direction A1 through the optical dome 11b of the casing 11 that maintains the specific floating posture on the surface of the water W without fail.

As described above, in the first embodiment of the present invention, specific gravity of a capsule endoscope that includes an imaging unit fixed inside a capsule-shaped casing is set equal to or lower than the specific gravity of liquid introduced inside an organ of the subject, and a center of gravity of the capsule endoscope is set at a position deviated from the center of this casing and on the opposite side to the imaging unit, thereby making the casing take a specific floating posture when the casing floats on the surface of the liquid. The optical characteristics of this imaging unit are set depending on an object present in an imaging direction that is determined by the specific floating posture that this casing maintains. Therefore, it is possible to focus on a portion near an object in air that is positioned far away compared to that in the case where the inside of an organ is imaged from a short distance, and is possible to take the object in air positioned inside a focus area of this imaging unit in an imaging field of view in a wide range properly. As a result, it is possible to provide a capsule endoscope that can properly take a clear image of the inside of an organ in a wide range in a state where the capsule endoscope floats on the surface of liquid introduced inside an organ whose inner space is large, such as stomach.

Next, a second embodiment of the present invention is explained. While in the first embodiment described above, the single imaging unit 13 is fixed at a position opposite to the center of gravity G of the capsule endoscope 2 relative to the center C of the casing 11 inside the casing 11, in the second embodiment, a binocular capsule endoscope in which imaging units are respectively fixed on the opposite side and the identical side (center of gravity side) of the center of gravity of the capsule endoscope relative to the center of a casing is used.

Figure 4:
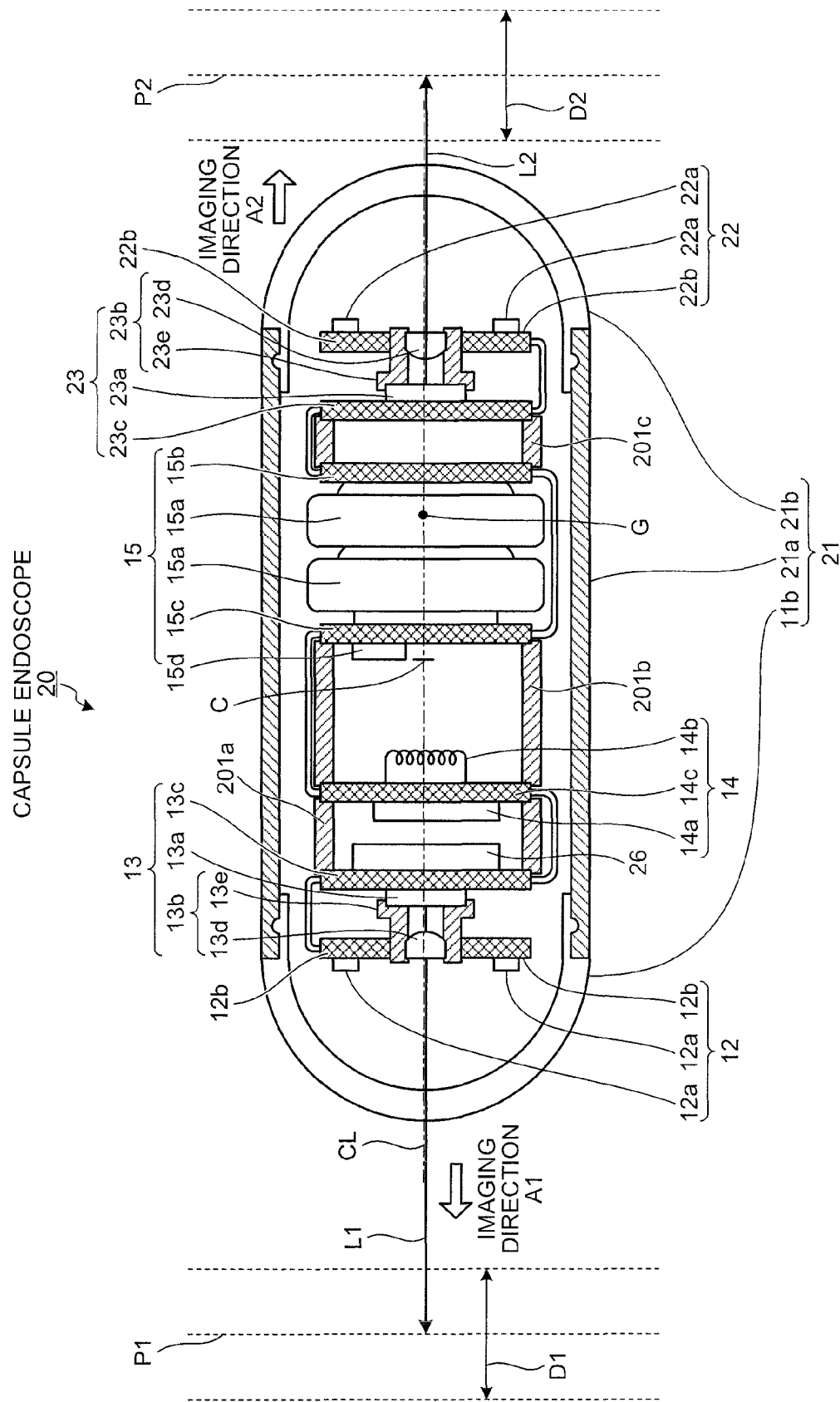
FIG. 4 is a side cross-section schematically showing a constitutional example of a capsule endoscope according to a second embodiment of the present invention.

FIG. 4 is a side cross-section schematically showing a constitutional example of a capsule endoscope according to the second embodiment of the present invention. As shown in FIG. 4, a capsule endoscope 20 according to the second embodiment includes a casing 21 in place of the casing 11 of the capsule endoscope 2 according to the first embodiment described above, and a control unit 26 in place of the control unit 16. The capsule endoscope 20 further includes an illuminating unit 22 and an imaging unit 23. In this case, the wireless communication unit 14 transmits a radio signal including an in-vivo image that is taken by the imaging unit 13 and a radio signal including an in-vivo image of the subject that is taken by the imaging unit 23 to the external receiving apparatus 3 alternately by wireless communication. An in-vivo information acquiring system according to the second embodiment includes the capsule endoscope 20 in place of the capsule endoscope 2 according to the first embodiment described above. Other components are the same as those of the first embodiment, and like reference characters refer to like parts.

The casing 21 is a capsule-shaped casing that is formed in a size easy to be introduced inside the subject, in nearly the same manner as the casing 11 of the capsule endoscope 2 according to the first embodiment described above. Specifically, the casing 21 is formed with a tubular casing main body 21a and optical domes 11b and 21b.

The casing main body 21a is a tubular case in which one end is open, and houses therein the respective components of the capsule endoscope 20, such as the illuminating units 12 and 22, the imaging units 13 and 23, the wireless communication unit 14, the power source unit 15, and the control unit 26. In this case, near one of the openings of the casing main body 21a, the illuminating unit 12 and the imaging unit 13 described above are arranged in a fixed manner, and near the other opening, the illuminating unit 22 and the imaging unit 23 are arranged in a fixed manner. Furthermore, in an internal area that is sandwiched between a set of the illuminating unit 12 and the imaging unit 13 and a set of the illuminating unit 22 and the imaging unit 23, the wireless communication unit 14, the power source unit 15, and the control unit 26 are arranged.

The optical dome 11b is a transparent dome-shaped optical member as described above, and on the outer surface of the optical dome 11b, a transparent water-drop protective film, such as a water-repellent transparent film and a hydrophilic transparent film, is formed. The optical dome 11b thus structured is attached at an opening end being one end of the casing main body 21a, specifically, an opening end on a side on which the illuminating unit 12 and the imaging unit 13 are fixed, and closes this opening end. On the other hand, although the optical dome 21b is a dome-shaped transparent optical member, a water-drop protective film is not formed on an outer surface thereof. The optical dome 21b is attached at the other opening of the casing main body 21a, specifically, an opening end on a side on which the illuminating unit 22 and the imaging unit 23 are fixed, and closes the other opening end.

The casing 21 thus configured with the optical domes 11b and 21b on both sides houses the respective components (the illuminating unit 12, 22, the imaging unit 13, 23, the wireless communication unit 14, the power source unit 15, the control unit 16, etc.) of the capsule endoscope 20 in a fluid-tight manner.

The illuminating unit 22 functions as an illuminating means for illuminating the inside (that is, an object of the imaging unit 23) of an organ of the subject to be imaged by the imaging unit 23. Specifically, the illuminating unit 22 is arranged on a side of the optical dome 21b in the casing 21, and illuminates an object of the imaging unit 23 through the optical dome 21b. This illuminating unit 22 has a plurality of light emitting devices 22a that emit illumination light to an object of the imaging unit 23, and an illumination board 22b on which a circuit to implement the function of the illuminating unit 22 is formed. The illuminating unit 12 of the capsule endoscope 20 is arranged on a side of the optical dome 11b inside the casing 21, and illuminates an object in the imaging direction A1 (namely, an object of the imaging unit 13) as described above.

The light emitting devices 22a are mounted on the illumination board 22b, and emit illumination light to an imaging field of view of the imaging unit 23 through the optical dome 21b. The light emitting devices 22a illuminate an object of the imaging unit 23 (that is, the inside of an organ of the subject) with the illumination light. These light emitting devices 12a emit illumination light of a sufficient emitting amount (specifically, small emitting amount compared to the light emitting devices 12a of the imaging unit 12 described above) for illuminating an object that is imaged from a short distance by the imaging unit 23. The illumination board 22b is, for example, a rigid circuit board that is formed in a disc shape, and is arranged on a side of the optical dome 21b in the casing 21. In a central part of the illumination board 22b, a lens frame of the imaging unit 23 described later is inserted.

The imaging unit 23 functions as an imaging means that takes an image of an object (inside of an organ of the subject) illuminated by the illuminating unit 22. Specifically, the imaging unit 23 is fixed on a side of the optical dome 21b inside the casing 21, and takes an image of an object in an imaging direction A2 that is determined by posture (in detail, floating posture of the casing 21 that floats on the surface of liquid) of the casing 21. The imaging direction A2 is, for example, the opposite direction to the imaging direction A1 of the imaging unit 13 described above. The imaging unit 23 has a solid-state imaging device 23a such as CCD and CMOS, an optical system 23b that images the image of an object on a light receiving surface of the sold-state imaging device 23a, and an imaging board 23c on which a circuit that implements the function of the imaging unit 23 is formed. The imaging unit 13 of the capsule endoscope 20 is fixed on a side of the optical dome 11b inside the casing 11, and takes an image of an object (for example, the inside of an organ in air) in the imaging direction A1, as described above.

The solid-state imaging device 23a captures an image of an object that is illuminated by the illuminating unit 22. Specifically, the solid-state imaging device 23a has an imaging field of view in the imaging direction A2 determined by the floating posture of the casing 21, and captures an image of the inside of an organ (that is, an object) inside the imaging field of view illuminated by the illuminating unit 22. Further specifically, the solid-state imaging device 23a has a light receiving surface that receives light from an object that is positioned in the imaging field of view, and performs photoelectric conversion on light from the object received through this light receiving surface to capture an image of the object (that is, an in-vivo image of the subject). Optical characteristics such as a light receiving amount of the solid-state imaging device 23a are set depending on an object in the imaging direction A2.

The optical system 23b includes a lens 23d that images an image of an object on the light receiving surface of the solid-state imaging device 23a, and a lens frame 23e that holds this lens 23d. The lens 23d collects light from the object present in the imaging direction A2 on the light receiving surface of the solid-state imaging device 23a, and images the image of the object on the light receiving surface of the solid-state imaging device 23a. Optical characteristics such as focal length and depth of field of the lens 23d are set depending on an object in the imaging direction A2.

The lens frame 23e has a tubular structure in which both ends are open, and holds the lens 23d inside a tubular portion thereof. Specifically, the lens frame 23e holds the lens 23d inside the tubular portion near an opening at one end. Moreover, the other end of the lens frame 23e is fixed to the solid-state imaging device 23a in so as to guide light from an object onto the light receiving surface of the solid-state imaging device 23a. The lens frame 23e holds the lens 23d at a position in a predetermined distance from the solid-state imaging device 23a described above. Distance between the solid-state imaging device 23a and the lens 23d that is defined by the lens frame 23e is set depending on an object in the imaging direction A2. The one end of the lens frame 23e (on a side on which the lens 23d is held) is inserted to the illumination board 22b described above, and is fixed to the illumination board 22b.

The imaging board 23c is, for example, a rigid circuit board that is formed in a disc shape, and is arranged on a side of the optical dome 21b in the casing 21 in a fixed manner. Specifically, the imaging board 23c is fixed at a position near the illumination board 22b, and on a side of the center C of the casing 21 relative to this illumination board 22b. On the imaging board 23c, the solid-state imaging device 23a described above is mounted.

The wireless communication unit 14 includes the wireless unit 14a, the antenna 14b, and the wireless board 14c, and transmits a radio signal including an in-vivo image of an object that is taken by the imaging unit 13 and a radio signal including an in-vivo image of the subject that is taken by the imaging unit 23 to the external receiving apparatus 3 alternately by wireless communication. In this case, the wireless unit 14a generates a radio signal including an in-vivo image of the subject that is taken by the imaging unit 13 and a radio signal including an in-vivo image of the subject that is taken by the imaging unit 23 alternately, and sequentially outputs the generated radio signals to the antenna 14b. The antenna 14b alternately transmits the radio signals generated by the wireless unit 14a, namely, the radio signal including an in-vivo image of the subject that is taken by the imaging unit 13 and the radio signal including an in-vivo image of the subject that is taken by the imaging unit 23.

The power source unit 15 is arranged on a side of the optical dome 21b in the casing 21, and supplies driving power to the respective components (namely, the illuminating units 12 and 22, the imaging units 13 and 23, the wireless communication unit 14, the control unit 16, etc.) of the capsule endoscope 20 according to the second embodiment.

The control unit 16 is mounted, for example, on the imaging board 13c, and controls the respective components of the capsule endoscope 20 according to the second embodiment. Specifically, the control unit 16 controls the light emitting devices 12a and 22a of the illuminating units 12 and 22, the solid-state imaging devices 13a and 23a of the imaging units 13 and 23, and the wireless unit 14a of the wireless communication unit 14. In this case, the control unit 26 controls operation timing of the light emitting devices 12a and the solid-state imaging devices 13a, similarly to the control unit 16 of the capsule endoscope 2 according to the first embodiment. Moreover, the control unit 26 controls operation timing of the light emitting devices 22a and the solid-state imaging device 23a so that the solid-state imaging device 23a captures an image of the object at predetermined time intervals in synchronization with the light emitting operation of the light emitting devices 22a. The control unit 26 performs the control to the light emitting device 12a and the solid-state imaging devices 13a and the control to the light emitting device 22a and the solid-state imaging devices 23a, alternately at predetermined time intervals. The control unit 16 has various kinds of parameters related to an image processing such as white balance, and has an image processing function of alternately generating image signals that include respective images of the object captured by the solid-state imaging devices 13a and 23a alternately. Moreover, the control unit 16 transmits the image signals including in-vivo images of the subject to the wireless communication unit 14 alternately, and controls the wireless unit 14a to generate and output the radio signal including the in-vivo images of the subject.

Next, the specific gravity and the center of gravity of the capsule endoscope 20 according to the second embodiment are explained. The capsule endoscope 20 has such a configuration that the illuminating units 12 and 22, the imaging units 13 and 23, the wireless communication unit 14, the power source unit 15, and the control unit 26 are housed in the casing 21 in a capsule form, as described above (see FIG. 4). The capsule endoscope 20 having such a configuration floats on the surface of liquid that is introduced inside an organ of the subject. In other words, the specific gravity of the capsule endoscope 20 is set to be lower than the specific gravity of a predetermined liquid (for example, water) that is introduced inside an organ of the subject.

Specifically, the specific gravity of the capsule endoscope 20 that floats on the surface of liquid is obtained, for example, by forming empty space equal to or larger than a predetermined volume inside the casing 21 or by providing a float member (not shown) to the casing 21. If the liquid introduced inside an organ of the subject is water, for example, the capsule endoscope 20 is arranged to have the specific gravity equal to or lower than the specific gravity of water (=1). It is preferable that the capsule endoscope 20 have the specific gravity with which a part (for example, the optical dome 11b) of the capsule endoscope 20 floating on the surface of the liquid introduced inside an organ of the subject is out of this liquid.

On the other hand, the center of gravity of the capsule endoscope 20 is set so that the floating posture of the capsule endoscope 20 in a state where the capsule endoscope is floating on the surface of liquid, that is the floating posture of the casing 21 is maintained in a specific posture. Specifically, as shown in FIG. 4, the center of gravity G of the capsule endoscope 20 is set at a position deviated from the center C of the casing 21 by arranging the battery 15a of the power source unit 15 or the like on a side of the dome portion 21b inside the casing 21 relative to the center C of the casing 21, for example. In this case, the center of gravity G is set on the side of the dome portion 21b (on a side of the imaging unit 23) relative to the center C of the casing 21, that is, on the opposite side to the imaging unit 13 described above but on the same side as the imaging unit 23. It is preferable that the center of gravity be set at a position deviated from the center C of the casing 21 to the side of the optical dome 21b (side of the imaging unit 23) and on or near the center axis CL. In other words, the imaging unit 13 is fixed at a position inside the casing 21 on the opposite side to the center of gravity G relative to the center C of the casing 21, and the imaging unit 23 is fixed at a position inside the casing 21 on the same side as the center of gravity G (center of gravity side) relative to the center C of the casing 21.

To set the specific gravity and the center of gravity of the capsule endoscope 20 as described above, it is required to appropriately arrange the respective components in the capsule endoscope 20. However, an appropriate arrangement of the respective components cannot be maintained just by folding a circuit board electrically connected through a flexible substrate. For this reason, a spacer is provided between the components so that the appropriate arrangement of the respective components is maintained easily. Specifically, as shown in FIG. 4, a spacer 201a is arranged between the imaging board 13c and the wireless board 14c, a spacer 201b is arranged between the wireless board 14c and the power source board 15c, and a spacer 201bc is further arranged between the power source board 15b and the imaging board 23c so that intervals are appropriately kept between circuit boards. As a result, the appropriate arrangement of the respective components required to set the specific gravity and the center of gravity of the capsule endoscope 20 is achieved with ease. By using MID (molded interconnect device) as the spacer, the spacer can serve as both the flexible substrate and the spacer.

By thus setting the center of gravity G of the capsule endoscope 20 at a position deviated from the center C of the casing 21, the floating posture of the casing 21 in a state where the capsule endoscope 20 is floating on the surface of liquid can be maintained in a specific floating posture. Specifically, the floating posture of the casing 21 is maintained in such a specific floating posture that the imaging direction A1 of the imaging unit 13 is directed upward of the liquid (liquid in which the capsule endoscope 20 floats), while the imaging direction A2 of the imaging unit 23 is directed downward of the liquid (that is, under the liquid).

The imaging unit 13 described above is arranged such that the optical axis (that is, optical axis of the lens 13d) of the imaging unit 13 corresponding to the imaging direction A1 is parallel to or on the same straight line as the center axis CL in the longitudinal direction of the casing 21 in a fixed manner. Moreover, the imaging unit 23 described above is arranged such that the optical axis (that is, optical axis of the lens 23d) of the imaging unit 23 corresponding to the imaging direction A2 is parallel to or on the same straight line as the center axis CL in a fixed manner. In other words, the respective optical axes of the imaging units 13 and 23 are parallel to each other or on the same straight line. In this case, by arranging the center of gravity G at such a position, the floating posture of the casing 21 is maintained in the specific posture in which the imaging direction A1 of the imaging unit 13 is directed substantially vertically upward and the imaging direction A2 of the imaging unit 23 is directed substantially vertically downward.

A subject in the imaging direction A1 determined by the floating posture of the casing 21 is an object in air that is positioned above the liquid in which the capsule endoscope 20 floats. In this case, the imaging unit 13 described above captures an image of the object in air present in the imaging direction A1 through the optical dome 11b similarly to the first embodiment described above. On the other hand, an object in the imaging direction A2 determined by the floating posture of the casing 21 is an object under liquid that is positioned below the liquid in which the capsule endoscope 20 floats. In this case, the imaging unit 23 described above captures an image of the object under the liquid present in the imaging direction A2 through the optical dome 21b.

Next, optical characteristics of the imaging unit 213 that images an object in the imaging direction A2 determined by the floating posture of the casing 21 are explained. The optical characteristics of the imaging unit 13 that images an object in the imaging direction A1 are determined depending on the object in air present in the imaging direction A1 similarly to the first embodiment described above.

The imaging unit 23 images an object present in the imaging direction A2 determined by the floating posture of the casing 21 when the capsule endoscope 20 floats on the surface of liquid introduced inside an organ of the subject as described above. In this case, the imaging unit 23 images the object under the liquid present in the imaging direction A2 through the optical dome 21b. The optical characteristics of the imaging unit 23 are set depending on an object (subject under the liquid) in the imaging direction A2 that is determined by the floating posture of the casing 21. The optical characteristics of the imaging unit 23 include an image forming property that determines a position of a focal point in the imaging direction A2, depth of field at the focal point in the imaging direction A2, an angle of view that defines the imaging field of view of the imaging unit 23, a light receiving amount when an image of the object is imaged, and the like.

The imaging forming property of the imaging unit 23 is an optical characteristic to determine the focal point of the imaging direction A2, and is set, for example, by adjusting a distance between the solid-state imaging device 23a and the lens 23d, and the focal length of the lens 23d. As the image forming property of the imaging unit 23, the focal point is set at a point P21 that is distant from the imaging unit 23 by a distance L2 in the imaging direction A2, as shown in FIG. 4. The distance L2 in the imaging direction A2 is shorter than the distance L1 in the imaging direction A1 described above, and is substantially equal to an object distance (a distance from the imaging unit 23 to the inner wall of an organ in the liquid) when an object in the liquid that is present under the liquid introduced inside an organ of the subject is imaged from a short distance. By thus setting the focal point at a position P2 in the imaging direction A2, the imaging unit 23 of the capsule endoscope 20 in a floating state on the surface of the liquid inside the organ can focus at a position near the object in liquid present under the liquid (specifically, near an inner wall of the organ in liquid).

The distance L1 in the imaging direction A1 is longer than the distance L2 in the imaging direction A2. Therefore, as the image forming property of the imaging unit 13, the focal point is set at a point far away compared to the imaging forming property of the imaging unit 23 that images an object in liquid from a short distance.

Depth of field D2 of the imaging unit 23 is set by adjusting the distance between the solid-state imaging device 23a and the lens 23d, the focal length of the lens 23d, the distance L2 in the imaging direction A2, and the like. The depth of field D2 thus set is set to have a predetermined range from the point P2 in the imaging direction A2 as the center as shown in FIG. 4. Specifically, the depth of field D2 is set such that the object in liquid that is present in the imaging direction A2 is positioned inside a region between a near point and a far point of the imaging unit 23, considering the position of the surface of liquid inside an organ of the subject and a stretching action of the organ.

The angle of view of the imaging unit 23 defines the imaging field of view of the imaging unit 23, and is set, for example, by adjusting the distance between the solid-state imaging device 23a and the lens 23d, the focal length of the lens 23d, the light receiving surface of the solid-state imaging device 23a, and the like. The angle of view of the imaging unit 23 is set so as to take an object in liquid inside the imaging field of view substantially similarly to the case where the inside of an organ whose inner space is small, such as esophagus and small intestine, are imaged from a short distance. The angle of view of the imaging unit 13 described above can be set an angle of view equivalent to that of the imaging unit 23 suitable for imaging from a short distance; however, it is preferable that the angle of view be set wider than that of the imaging unit 23.

The light receiving amount of the imaging unit 23 when an image of an object is captured is set to a substantially equivalent amount to that in the case of imaging the inside of an organ whose inner space is small such as esophagus and small intestine from a short distance. Specifically, the light emitting devices 22a of the illuminating unit 22 described above emits illumination light in a light emitting amount sufficient to illuminate an object in liquid that is present in the imaging direction A2. As the light receiving amount of the imaging unit 23 (specifically, the solid-state imaging device 23a), light receiving sensitivity thereof is set suitably for receiving reflection light from the object in liquid that occurs when the object in liquid is irradiated by the illumination light of the light emitting devices 22a. The light emitting amount of the light emitting device 12a described above is larger than that of the light emitting devices 22a that illuminate an object in liquid.

Figure 5:
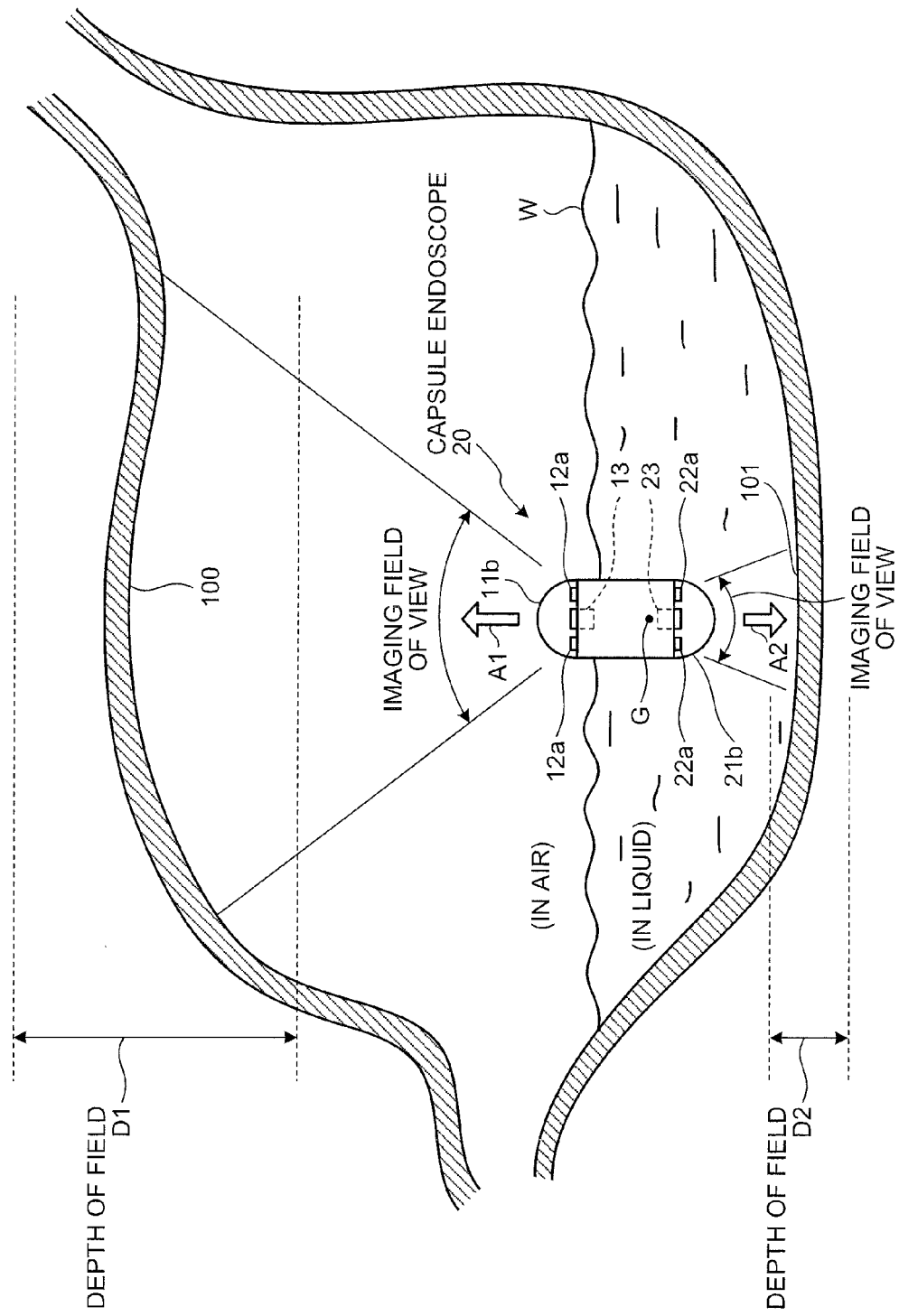
FIG. 5 is a schematic diagram for explaining operation of the capsule endoscope that images the inside of stomach alternately in air and in liquid in a state where the capsule endoscope is floating on the surface of the liquid inside the stomach of a subject.

Next, operation of the capsule endoscope 20 that takes an image of the inside of the stomach of the subject 1 in a state where the capsule endoscope 20 is floating in water when the capsule endoscope 20 and a required amount of water are introduced inside the stomach of the subject 1 as one example of organs whose inner space is large is explained. FIG. 5 is a schematic diagram for explaining operation of the capsule endoscope 20 that images the inside of stomach in air and in liquid alternately, in a floating state on the surface of water inside the stomach of the subject 1.

First, the capsule endoscope 20 is taken in through the mouth of the subject 1 with a required amount of water, to be introduced inside the stomach of the subject 1. In this case, because the capsule endoscope 20 is set to have the specific gravity equal to or lower than the specific gravity of water (for example, about 0.8), the capsule endoscope 20 floats on the surface of the water inside the stomach of the subject 1.

Thereafter, the capsule endoscope 20 in a floating state on the surface of the water takes images of the inside of the stomach in air with the imaging unit 13 and the inside of the stomach in liquid by the imaging unit 23, maintaining the specific floating posture. In this case, the capsule endoscope 20 takes an image of the inside of the stomach in air and an image of the inside of the stomach in liquid alternately.

Specifically, as shown in FIG. 5, the capsule endoscope 20 set to have the specific gravity equal to or lower than that of water floats on the surface of a required amount of the water W that is introduced inside the stomach of the subject 1 and takes the specific floating posture. The center of gravity G of the capsule endoscope 20 is set at a position deviated from the center C of the casing 21 and opposite to the imaging unit 13 relative to the center C (preferably, on the center axis CL) as described above. When the center of gravity G is set at such a position, the capsule endoscope 20 in a floating state takes the specific floating posture at the surface of the water W, that is, the floating posture in which the optical dome 11b is out of the water surface and the optical dome 21b is under the water. In this case, the casing 21 maintains such a floating posture that the imaging direction A1 of the imaging unit 13 is directed upward from the water W similarly to the case of the first embodiment described above, and that the imaging direction A2 of the imaging unit 23 is directed downward under the surface of the water W (in liquid), by the center of gravity G.

By such a floating posture of the casing 21, the imaging direction A1 of the imaging unit 13 is determined to be upward from the water W (for example, vertically upward), and the imaging direction A2 of the imaging unit 23 is determined to be downward from the water W (for example, vertically downward). The imaging unit 23 takes an image of an object in liquid that is positioned in the imaging direction A2 determined by the floating posture of the casing 21. Specifically, the light emitting devices 22a sufficiently illuminate an inside of stomach 101 in liquid being the object in the imaging direction A2. The imaging unit 23 captures an image of the inside of stomach 101 that is sufficiently illuminated by the light emitting devices 22a from a short distance.

The optical characteristics of the imaging unit 23 are set depending on an object (namely, the inside of stomach 101 in liquid) in the imaging direction A2 that is determined by the floating posture of the casing 21. Specifically, as the image forming property of the imaging unit 23, the focal point is set near the object in liquid present in the imaging direction A2, that is, near a wall of the inside of stomach 101 in liquid. In this case, the distance between the solid-state imaging device 23a and the lens 23d, the focal length of the lens 23d, and the like are adjusted so that the distance L2 in the imaging direction A2 described above is substantially equal to a distance (subject distance) from the imaging unit 23 of the capsule endoscope 20 that is floating in on the surface of the water W to the inside of stomach 101 in liquid.

The depth of field D2 of the imaging unit 23 is set such that the inside of stomach 101 in liquid is positioned inside a region between a near point and a far point of the imaging unit 23 in the imaging direction A2 (that is, a focus area of the imaging unit 23). The angle of view of the imaging unit 23 is set suitably for taking the inside of stomach 101 in liquid that is present inside the focus range of the imaging unit 23 from a short distance. The light receiving amount of the imaging unit 23 is set a light receiving sensitivity suitable for receiving reflection light from the inside of stomach 101 in liquid that is generated when the inside of stomach 101 in liquid is irradiated by illumination light of the light emitting devices 22a described above.

The imaging unit 23 whose optical characteristics are set depending on an object (the inside of stomach 101 in liquid) in the imaging direction A2 as described above takes the inside of stomach 101 in liquid that is positioned inside the focus area in the imaging field of view that is determined by the angle of view. Furthermore, the inside of stomach 101 in liquid taken in the imaging field of view of the imaging unit 23 is sufficiently illuminated by the light emitting device 22a. Accordingly, the imaging unit 23 can capture a clear image of the inside of stomach 101 in liquid present in the imaging direction A2 through the optical dome 21b of the casing 11 that maintains the specific floating posture on the surface of the water W without fail.

The imaging unit 13 can capture a wide range and clear image of an object (the inside of stomach 100 in air) in the imaging direction A1 that is determined by the floating posture of the casing 21 on the surface of the water W properly, similarly to the case in the first embodiment described above.

As described above, in the second embodiment of the present invention, specific gravity of a capsule endoscope that has a configuration in which a first imaging unit and a second imaging unit are arranged inside a capsule-shaped casing is set equal to or lower than the specific gravity of liquid introduced inside an organ of the subject, and a center of gravity of the capsule endoscope is set at a position that is deviated from the center of this casing and that satisfies both conditions that it is on the opposite side to the first imaging unit and it is on the same side as the second imaging unit, thereby making the casing take a specific floating posture when the casing floats on the surface of the liquid inside an organ of the subject. The optical characteristics of the first imaging unit are set depending on an object present in an imaging direction of the first imaging unit that is determined by the specific floating posture that this casing maintains, and the optical characteristics of the second imaging unit are set depending on an object present in liquid present in the imaging direction of the second imaging unit determined by the specific floating posture that the casing maintains. Therefore, similarly to the first embodiment described above, it is possible to take the object in air positioned inside a focus area of the first imaging unit in an imaging field of view in a wide range properly, and it is possible to take the object in liquid positioned inside a focus area of the second imaging unit properly. As a result, in addition to the effect of the first embodiment described above, it is possible to take a clear image of the inside of an organ in liquid from a short distance, and to provide a capsule endoscope that can properly take a clear image of the inside of an organ in liquid and that can efficiently take a clear image of the inside of an organ whose inner space is large, such as stomach in a short time.

Next, a third embodiment of the present invention is explained. While in the second embodiment described above, the center of gravity G of the capsule endoscope 20 is set on the center axis CL of the casing 21, and the imaging direction A1 of the imaging unit 13 is set parallel to the center axis CL of the casing 21, in the third embodiment, the center of gravity of a capsule endoscope is set at a position that is further deviated from the center axis CL, and the imaging direction of the imaging unit 13 is set in a direction slanted toward the opposite side to the center of gravity G relative to the center axis CL in the longitudinal direction of a casing.

Figure 6:
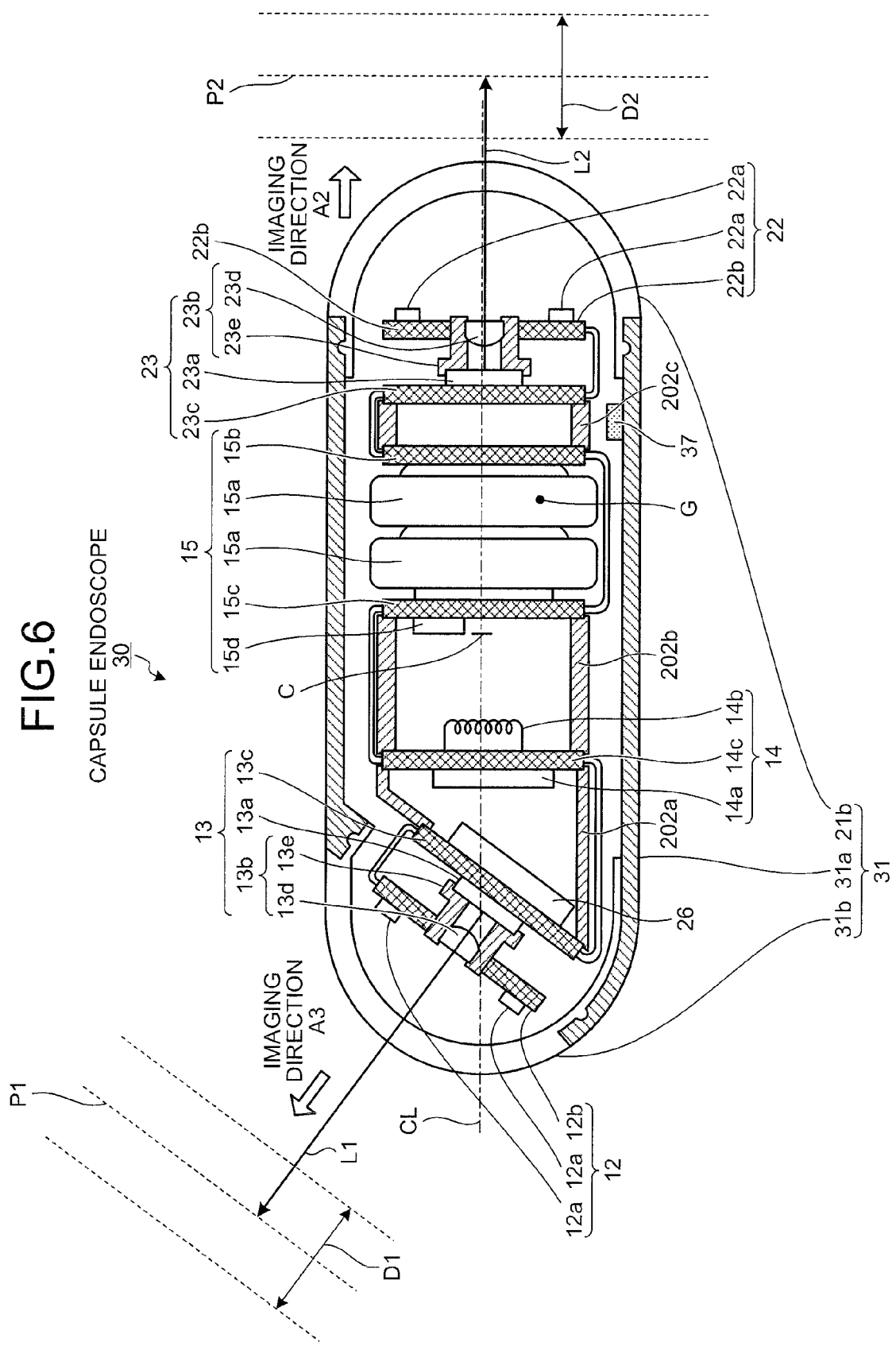
FIG. 6 is a side cross-section schematically showing a constitutional example of a capsule endoscope according to a third embodiment of the present invention.

FIG. 6 is a side cross-section schematically showing a constitutional example of a capsule endoscope according to the third embodiment of the present invention. As shown in FIG. 6, a capsule endoscope 30 according to the third embodiment includes a casing 31 in place of the casing 21 of the capsule endoscope 20 according to the second embodiment described above, and the capsule endoscope 30 further includes a spindle member 37 to adjust the position of the center of gravity of the capsule endoscope 30. In this case, an imaging direction A3 of the imaging unit 13 is set to a direction slanted toward the opposite side to the center of gravity G relative to the center axis CL of the casing 31. An in-vivo information acquiring system according to the third embodiment includes the capsule endoscope 30 in place of the capsule endoscope 20 according to the second embodiment described above. Other components are the same as those of the second embodiment, and like reference characters refer to like parts.

The casing 31 is a capsule-shaped casing that is formed in a size easy to be introduced inside the subject, in nearly the same manner as the casing 21 of the capsule endoscope 20 according to the second embodiment described above. Specifically, the casing 31 is formed with a tubular casing main body 31a and optical domes 21b and 31b.

The casing main body 31a is a tubular casing in which both ends are open. In detail, the casing main body 31a has an opening end (slanted opening end) that opens in a direction slanted toward the opposite side to the center of gravity G of the capsule endoscope 30 relative to the center axis CL in the longitudinal direction of the casing 31 at one end, and has an opening end that opens in the same direction as the center axis CL at the other end. The casing main body 31a thus structured houses therein the respective components of the capsule endoscope 30, such as the illuminating units 12 and 22, the imaging units 13 and 23, the wireless communication unit 14, the power source unit 15, the control unit 26, and the spindle member 37. In this case, near one of the opening ends of the casing main body 31a, the illuminating unit 12 and the imaging unit 13 described above are arranged in a fixed manner, and near the other one of the opening ends, the illuminating unit 22 and the imaging unit 23 are arranged in a fixed manner. Furthermore, in an internal area that is sandwiched between a set of the illuminating unit 12 and the imaging unit 13 and a set of the illuminating unit 22 and the imaging unit 23, the wireless communication unit 14, the power source unit 15, and the control unit 26 are arranged. Further, near the other one of the opening ends of the casing main body 31a, the spindle member 37 is arranged in a fixed manner.

The optical dome 31b is a transparent dome-shaped optical member, and is attached at the slanted opening end (the opening end at which the illuminating unit 12 and the imaging unit 13 are fixed) of the casing main body 31a and closes this slanted opening end. On the outer surface of the optical dome 31b, a transparent water-drop protective film, such as a water-repellent transparent film and a hydrophilic transparent film, is formed similarly to the optical dome 11b described above. The optical dome 21b is attached at the other opening end of the casing main body 31a, specifically, the opening end on a side on which the illuminating unit 22 and the imaging unit 23 are fixed, and closes this opening end.

The casing 31 thus configured with the optical domes 21b and 31b on both sides houses the respective components (the illuminating unit 12, 22, the imaging unit 13, 23, the wireless communication unit 14, the power source unit 15, the control unit 16, the spindle member 37, etc.) of the capsule endoscope 30 in a fluid-tight manner.

The imaging unit 13 that is fixed inside the casing 31 (specifically, near the slanted opening end of the casing main body 31a) directs an imaging direction A3 to a direction that is slanted toward the opposite side to the center of gravity G of the capsule endoscope 30 relative to the center axis CL of the casing 31, instead of the imaging direction A1 described above. In this case, the optical axis (namely, the optical axis of the lens 13d) of the imaging unit 13 is slanted toward the opposite side to the center of gravity G of the capsule endoscope 30 relative to the center axis CL of the casing 31. Optical characteristics of the imaging unit 13 are set depending on an object in the imaging direction A3. In this case, the optical characteristics of the imaging unit 13 are set in a similar manner as in the case where an object in the imaging direction A1 is imaged described above, except that the imaging direction is changed from the imaging direction A1 described above to the imaging direction A3. Therefore, similarly to the case of the imaging direction A1 described above, the imaging unit 13 captures an image of an object in air that is present in the imaging direction A3.

The illuminating unit 12 (specifically, the light emitting devices 12a) that is fixed near the slanted opening end of the casing main body 31a sufficiently illuminate an imaging field of view of the imaging unit 13, that is, an object present in the imaging direction A3, similarly to the case of the object in air in the imaging direction A1 described above.

The spindle member 37 is to adjust the position of the center of gravity G of the capsule endoscope 30. Specifically, the spindle member 37 is arranged in a fixed manner near the other one of the opening ends of the casing main body 31a, that is, near the opening end at which the optical dome 21b is mounted, for example. The weight of the spindle member 37 is light enough to keep the specific gravity of the capsule endoscope 30 equal to or lower than the specific gravity of liquid (for example, water) that is introduced inside an organ of the subject even when the spindle member 37 is arranged inside the casing 31 in a fixed manner. The spindle member 37 thus structured enables the capsule endoscope 30 to maintain the specific gravity equal to or lower than the liquid, an shifts the center of gravity G of the capsule endoscope 30 to a position deviated from the center axis CL of the casing 31.

Next, the specific gravity and the center of gravity of the capsule endoscope 30 according to the third embodiment are explained. The capsule endoscope 30 has such a configuration that the illuminating units 12 and 22, the imaging units 13 and 23, the wireless communication unit 14, the power source unit 15, the control unit 26, and the spindle member 37 are housed in the casing 21 in a capsule form, as described above (see FIG. 6). The capsule endoscope 30 having such a configuration floats on the surface of liquid that is introduced inside an organ of the subject. In other words, the specific gravity of the capsule endoscope 30 is set to be equal to or lower than the specific gravity of a predetermined liquid (for example, water) that is introduced inside an organ of the subject.

Specifically, the specific gravity of the capsule endoscope 30 that floats on the surface of liquid is obtained, for example, by forming empty space equal to or larger than a predetermined volume inside the casing 31 or by providing a float member (not shown) to the casing 31. If the liquid introduced inside an organ of the subject is water, for example, the capsule endoscope 30 is arranged to have the specific gravity equal to or lower than the specific gravity of water (=1). It is preferable that the capsule endoscope 30 have the specific gravity with which a part (for example, the optical dome 31b) of the capsule endoscope 30 floating on the surface of the liquid introduced inside an organ of the subject is out of this liquid.

On the other hand, the center of gravity of the capsule endoscope 30 is set so that the floating posture of the capsule endoscope 30 in a state where the capsule endoscope is floating on the surface of liquid, that is the floating posture of the casing 31 is maintained in a specific posture. Specifically, as shown in FIG. 6, the center of gravity G of the capsule endoscope 30 is set at a position deviated from the center C of the casing 31 by arranging the battery 15a of the power source unit 15 or the like on a side of the dome portion 21b inside the casing 31 relative to the center C of the casing 31, and fixing the spindle member 37 near the opening end (the opening end at which the optical dome 21b is mounted) of the casing main body 31a, for example. In this case, the center of gravity G is set on the side of the dome portion 21b) relative to the center C of the casing 31, and deviated from the center axis CL toward the opposite side of the optical axis of the imaging unit 13 that is slanted with respect to the center axis CL. In other words, the imaging unit 13 is arranged in a fixed manner inside the casing 31 on the opposite side to the center of gravity G relative to the center C of the casing 31 in such a manner that the optical axis (the imaging direction A3) is slanted toward the opposite side to the center of gravity G relative to the center axis CL. The imaging unit 23 is fixed at a position inside the casing 31 on the same side as the center of G (center of gravity side) relative to the center C of the casing 31.

To set the specific gravity and the center of gravity of the capsule endoscope 30 as described above, it is required to appropriately arrange the respective components in the capsule endoscope 30. However, an appropriate arrangement of the respective components cannot be maintained just by folding a circuit board electrically connected through a flexible substrate. For this reason, a spacer is provided between the components so that the appropriate arrangement of the respective components is maintained easily. Specifically, as shown in FIG. 6, a spacer 202a is arranged between the imaging board 13c and the wireless board 14c, a spacer 202b is arranged between the wireless board 14c and the power source board 15c, and a spacer 202c is further arranged between the power source board 15b and the imaging board 23c so that intervals are appropriately kept between circuit boards. As a result, the appropriate arrangement of the respective components required to set the specific gravity and the center of gravity of the capsule endoscope 30 is achieved with ease. By using MID (molded interconnect device) as the spacer, the spacer can serve as both the flexible substrate and the spacer.

By thus setting the center of gravity G of the capsule endoscope 30 at a position deviated from the center axis CL, the floating posture of the casing 31 in a state where the capsule endoscope 30 is floating on the surface of liquid can be maintained in a specific floating posture. Specifically, the floating posture of the casing 23 is maintained in such a specific floating posture that the imaging direction A3 of the imaging unit 13 is directed upward of the liquid (liquid in which the capsule endoscope 30 floats), while the imaging direction A2 of the imaging unit 23 is directed downward of the liquid (that is, under the liquid).

The imaging unit 13 described above is arranged such that the optical axis (that is, optical axis of the lens 13d) of the imaging unit 13 corresponding to the imaging direction A3 is slanted toward the opposite side to the center of gravity G relative to the center axis CL in a fixed manner. Moreover, the imaging unit 23 described above is arranged such that the optical axis (that is, optical axis of the lens 23d) of the imaging unit 23 corresponding to the imaging direction A2 is parallel to or on the same straight line as the center axis CL in a fixed manner. In this case, by arranging the center of gravity G at such a position, the floating posture of the casing 21 is maintained in the specific posture in which the imaging direction A3 of the imaging unit 13 is directed upward of the liquid and the imaging direction A2 of the imaging unit 23 is directed under the liquid. By such floating posture of the casing 31, the imaging direction A3 of the imaging unit 13 is directed substantially vertically upward and the imaging direction A2 of the imaging unit 23 is directed substantially vertically downward from the surface of the liquid.

A subject in the imaging direction A3 determined by the floating posture of the casing 31 is an object in air that is positioned above the liquid in which the capsule endoscope 30 floats. In this case, the imaging unit 13 described above captures an image of the object in air present in the imaging direction A3 through the optical dome 31b similarly to the second embodiment described above. On the other hand, an object in the imaging direction A2 determined by the floating posture of the casing 31 is an object under liquid that is positioned below the liquid in which the capsule endoscope 30 floats. In this case, the imaging unit 23 described above captures an image of the object under the liquid present in the imaging direction A2 through the optical dome 21b.

Next, operation of the capsule endoscope 30 that takes an image of the inside of the stomach of the subject 1 in a state where the capsule endoscope 30 is floating in water when the capsule endoscope 30 and a required amount of water are introduced inside the stomach of the subject 1 as one example of organs whose inner space is large is explained. FIG. 7 is a schematic diagram for explaining operation of the capsule endoscope 30 that images the inside of stomach alternately in air and in liquid in a state where the capsule endoscope 30 is floating in an oblique position on the surface of the water inside the stomach of the subject 1.

First, the capsule endoscope 30 is taken in through the mouth of the subject 1 with a required amount of water, to be introduced inside the stomach of the subject 1. In this case, because the capsule endoscope 30 is set to have the specific gravity equal to or lower than the specific gravity of water (for example, about 0.8) and the center of gravity G deviated from the center axis CL of the casing 31, the capsule endoscope 30 floats obliquely on the surface of the water inside the stomach of the subject 1. Thereafter, the capsule endoscope 30 in a floating state on the surface of the water takes images of the inside of the stomach in air with the imaging unit 13 and the inside of the stomach in liquid by the imaging unit 23, maintaining the specific floating posture. In this case, the capsule endoscope 30 takes an image of the inside of the stomach in air and an image of the inside of the stomach in liquid alternately.

Specifically, as shown in FIG. 7, the capsule endoscope 30 set to have the specific gravity equal to or lower than that of water floats on the surface of a required amount of the water W that is introduced inside the stomach of the subject 1 and takes the specific floating posture. The center of gravity G of the capsule endoscope 30 is set at a position deviated from the center C of the casing 31 toward the opposite side to the imaging unit 13 relative to the center C and deviated toward the opposite side to the optical axis of the imaging unit 13 from the center axis CL as described above. The capsule endoscope 30 whose center of gravity G is set at such a position floats in the water W in a state where the center axis CL is oblique to the surface of the water W, and takes the specific floating posture in which the optical dome 31b is out of the water surface and the optical dome 21b is under the water. In this case, the casing 31 takes the floating posture (hereinafter, "oblique floating posture") in which the center axis CL is oblique to the surface of the water W, and maintains the oblique floating posture in which the imaging direction A3 of the imaging unit 13 is directed upward from the water W and the imaging direction A2 of the imaging unit 23 is directed downward under the surface of the water W (in liquid), by the center of gravity G.

By such a floating posture of the casing 31, the imaging direction A3 of the imaging unit 13 is determined to be upward from the water W (for example, vertically upward) similarly to the second embodiment. Meanwhile, the imaging direction A2 of the imaging unit 23 is determined to be downward from the water W. In this case, the imaging unit 13 can take a wide range and clear image of an object (the inside of stomach 100 in air) in the imaging direction A3 that is determined by the floating posture of the casing 31 on the surface of the water W properly, similarly to the case of the second embodiment. On the other hand, the imaging unit 23 can take a clear image of an object in liquid (the inside of stomach 101 in liquid) in the imaging direction A2 that is determined by the floating posture of the casing 31 on the surface of the water W from a short distance.

In the capsule endoscope 30 that takes respective images of the inside of stomach 100 in air and the inside of stomach 101 in liquid alternately with the imaging units 13 and 23, the center of gravity G is set as described above, and thus, the oblique floating posture (see FIG. 7) is maintained in which the imaging direction A3 is directed upward (in air) of the water W and the imaging direction A2 is directed downward of the water W (in liquid). Therefore, the required amount of the water W (amount of water introduced inside an organ of the subject) in which the capsule endoscope 30 floats in stomach, for example, can be less compared to the first and the second embodiments described above. As a result, the strain on the subject 1 of taking the capsule endoscope 30 and the water W can be reduced.

As described above, in the third embodiment of the present invention, a substantially the same configuration as the second embodiment is provided, and further, out of a first and a second imaging units that are arranged inside a casing in a fixed manner, an optical axis of the first imaging unit is slanted with respect to a center axis of the casing, and center of gravity of the capsule endoscope is set at a position deviated toward an opposite side to the first imaging unit from the center of the casing and deviated toward the opposite side to the optical axis of the first imaging unit from the center axis of the casing, thereby maintaining the casing in the oblique floating posture on the surface of liquid inside an organ of the subject. Therefore, an amount of liquid required for the casing to float therein inside an organ of the subject can be reduced. As a result, in addition to the effect of the second embodiment, it is possible to provide a capsule endoscope with which the strain on a subject can be reduced by reducing the amount of liquid to be introduced inside an organ of the subject.

Although in the first to the third embodiments of the present invention, the amount of illumination light to be emitted by the light emitting devices 12a of the illuminating unit 12 is large compared to the case of imaging from a short distance, it is not limited thereto. It can be arranged such that the amount of illumination light of the light emitting devices 12a can be substantially the same as that in the case of imaging from a short distance (specifically, illumination light that is emitted from the light emitting devices 22a of the illuminating unit 22 that illuminates an object in the imaging direction A2), and the light receiving sensitivity of the solid-state imaging device 13a of the imaging unit 13 that takes an image of an object in air is higher than that in the case of imaging from a short distance inside an organ.

Moreover, although in the first to the third embodiments, two units of the batteries 15a are connected to the power source unit 15, it is not limited thereto. As long as a required amount of driving power can be supplied to the respective components of the capsule endoscope according to the present invention, at least one unit of the battery 15a can be connected to the power source unit 15.

Furthermore, although in the first and the second embodiments of the present invention, the center of gravity of the capsule endoscope is set at a position deviated from the center of the casing by the arrangement of the battery 15a of the power source unit 15, it is not limited thereto. The center of gravity of the capsule endoscope can be set at a position deviated from the center of the casing by the arrangement of either one of the components (the illuminating unit, the imaging unit, the power source unit, the wireless communication unit, the control unit, etc.) constituting the capsule endoscope. Moreover, by additionally arranging a spindle member, a float member, or the like in the casing, the center of gravity of the capsule endoscope can be set to a position deviated from the center of the casing by the arrangement of the spindle member or the float member, or the center of gravity of the capsule endoscope can be set at a position deviated from the center of the casing by the arrangement of the components of the capsule endoscope, the spindle member, the float member, and the like combined.

Moreover, although in the third embodiment of the present invention, the center of gravity of the capsule endoscope is set at a position deviated from the center axis of the casing by the arrangement of the battery 15a of the power source unit 15 and the arrangement of the spindle member 37, it is not limited thereto. The center of gravity of the capsule endoscope can be set at a position deviated from the center axis of the casing by the arrangement of either one of the components (the illuminating unit, the imaging unit, the power source unit, the wireless communication unit, the control unit, etc.) of the capsule endoscope. Furthermore, by additionally arranging a spindle member, a float member, or the like in the casing, the center of gravity of the capsule endoscope can be set to a position deviated from the center axis of the casing by the arrangement of the spindle member or the float member, or the center of gravity of the capsule endoscope can be set at a position deviated from the center axis of the casing by the arrangement of the components of the capsule endoscope, the spindle member, the float member, and the like combined.

Moreover, although in the second and the third embodiments of the present invention, the center axis CL of the casing and the optical axis of the imaging unit 23 are arranged parallel to each other or positioned on the same straight line, it is not limited thereto. As the optical axis of the imaging unit 13 corresponding to the imaging direction A3 described above, the optical axis of the imaging unit 23 can be slanted with respect to the center axis CL of the casing. In this case, the optical axis of the imaging unit 23 can be slanted toward the opposite side to the center of gravity of the capsule endoscope, or can be slanted toward the center of gravity side. Further, the optical axis of the imaging unit 23 can be parallel to the optical axis of the imaging unit 13 corresponding to the imaging direction A3.

Furthermore, although in the first to the third embodiments of the present invention, the imaging unit is fixed near the opening end of the tubular casing main body that is one of the parts constituting the casing, it is not limited thereto. An opening can be formed in an intermediate part of the casing main body, and the imaging unit can be fixed near the opening at the intermediate part. In this case, at the opening at the intermediate part, an optical member that forms a part of the casing is mounted. Further, on the outer surface of the optical member, a transparent water-drop protective film such as a water-repellent film and a hydrophilic film can be formed.

Furthermore, in the first to the third embodiments of the present invention, the capsule endoscope acquires an internal body image by receiving, with the imaging device, light reflected from a wall of an organ obtained by emitting light thereon by the illuminating unit. Because reflection light from the surface of liquid is also received at this time, there is a problem that an acquired image can be unclear.

To solve this problem, it is required to prevent the surface of liquid from entering the angle of view of the imaging device and the light distribution angle of the illuminating unit. Thus, it is possible to prevent the imaging device from receiving the reflection light from the surface of liquid, and to provide a capsule endoscope that can acquire a clear internal body image.

For this, a configuration that enables an appropriate relation among the position and the angle of view of the imaging unit, the light distribution angle of the illuminating unit, and the specific gravity and the position of the center of gravity of the capsule endoscope is required. Such a configuration is described below.

A capsule endoscope that floats in liquid that is introduced inside a body in a state where the optical axis is perpendicular to the surface of the liquid is shown in FIGS. 8A and 8B. The specific gravity of the capsule endoscope to the liquid introduced inside the body is indicated by $\rho$. The volume of the capsule endoscope is divided to be in a ratio of $\rho:1-\rho$ to define a plane perpendicular to the optical axis. When the center of gravity of the capsule endoscope is far from the plane perpendicular to the optical axis than the center of the volume of a portion in which the volume ratio is $\rho$, and when a straight line that connects the center of gravity of the capsule endoscope and the center of the volume of the portion in which the volume ratio is $\rho$ is parallel to the optical axis, the capsule endoscope floats on the surface of the liquid in a state in which the optical axis of the imaging unit is perpendicular to the surface of the liquid. At this time, the surface of water is on the same plane as the plane perpendicular to the optical axis.

Figure 9A:
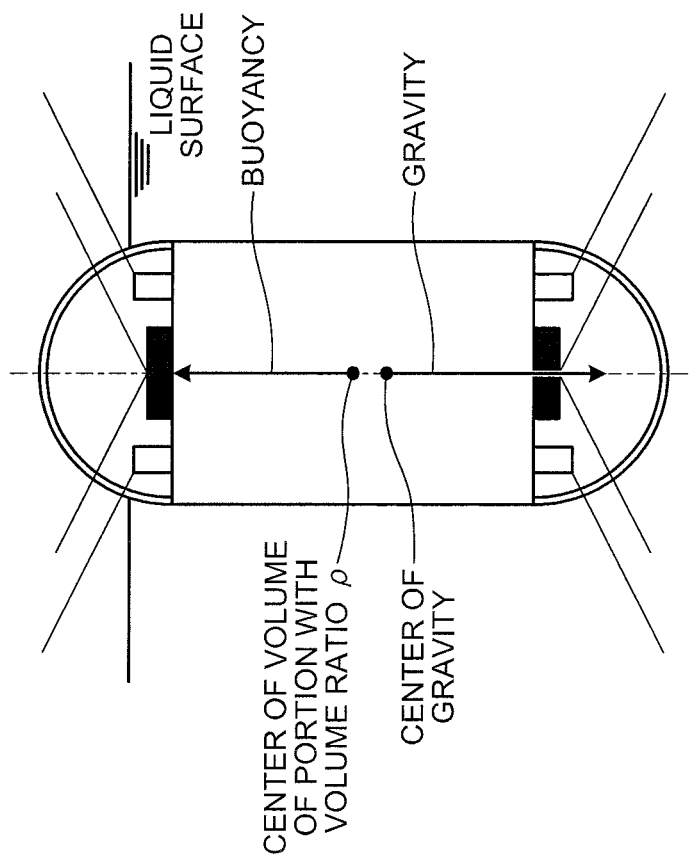
FIGS. 9A and 9B are schematic diagrams for explaining a principle of maintaining posture of the capsule endoscope in liquid.
Figure 9B:
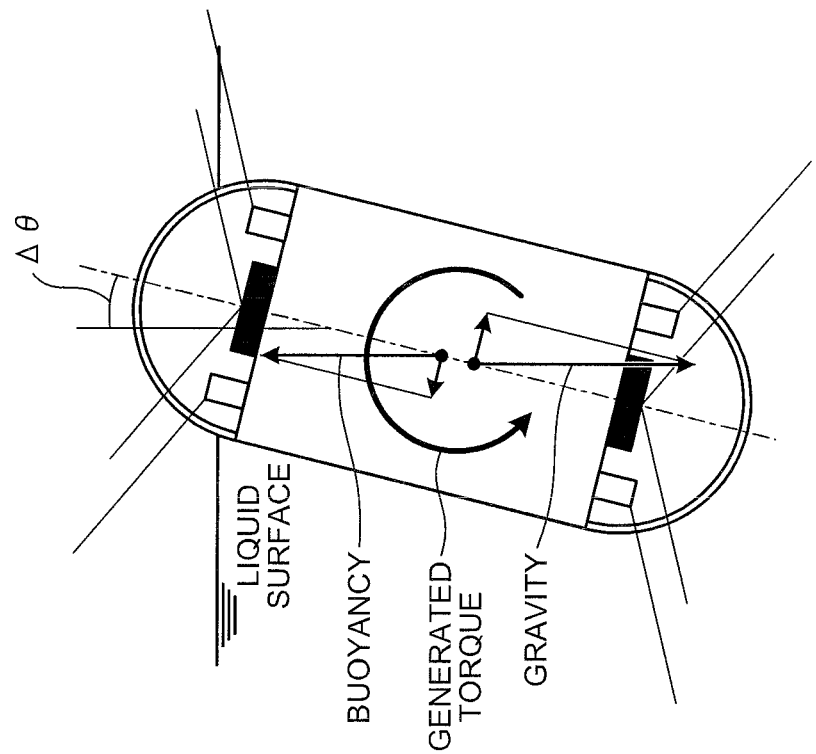

A principle that the capsule endoscope maintains the posture that satisfies the above conditions in liquid is explained referring to FIGS. 9A and 9B. The capsule endoscope floats in a state where the portion in which the volume ratio is $\rho$ is under water. At this time, to the center of gravity, gravity working on the capsule endoscope is applied, and to the center of the volume of the portion in which the volume ratio is $\rho$, buoyancy occurs, both in the vertical direction. However, because the center of the volume of the portion in which the volume ratio is $\rho$ and the center of gravity of the capsule endoscope are present on an identical straight line that is perpendicular to the surface of the liquid, torque that changes the posture of the capsule endoscope is not generated. On the other hand, when the posture of the capsule endoscope is slanted by $\Delta\theta$, torque is generated in a direction of bringing the posture of the capsule endoscope back to the original state by buoyancy and gravity. By this torque, the posture of the capsule endoscope is returned to the original posture naturally. When the capsule endoscope is slanted by $\Delta\theta$, the shape of the portion in which the volume ratio is $\rho$ changes in the actual situation, and along with this change, the position of the center of the volume changes. However, the amount of change is so small that the change does not affect this principle. Moreover, when the center of the volume of the portion in which the volume ratio is $\rho$ is farther distant from a plane dividing the capsule endoscope than the center of gravity of the capsule endoscope, if the capsule endoscope is slanted by $\Delta\theta$, torque is generated in the direction of further slanting the capsule endoscope. Accordingly, the capsule endoscope is further slanted and the posture thereof cannot be maintained.

Therefore, by setting the position of the imaging unit in the capsule endoscope, the position of the center of gravity, and the specific gravity such that the straight line connecting the center of the volume of the portion in which the volume ratio is ρ and the center of gravity of the capsule endoscope is parallel to the optical axis, a capsule endoscope that floats in a state where the optical axis of the capsule endoscope is perpendicular to the surface of liquid can be achieved for certain.

Furthermore, as shown in FIGS. 8A and 8B, by setting the position of the imaging unit such that the boundary of the field of view and the illumination boundary do not intersect, outside the capsule endoscope, with the plane that divides the capsule endoscope and that is perpendicular to the optical axis, it is possible to prevent entrance of the reflection light from the surface of water into the field of view, and reduction of the amount of light due to reflection of the illumination light on the surface of water. Therefore, a further clear image can be acquired.

Moreover, because the surface of liquid is in the horizontal direction and the optical axis of the imaging unit is always perpendicular to the surface of liquid, the imaging direction of the capsule endoscope can be determined to a unique direction. Therefore, a doctor can grasp the observation direction of the capsule endoscope, and therefore, diagnosis performance is improved.

Furthermore, a modification of the capsule endoscope that floats in liquid that is introduced into a body in a state where the optical axis of the imaging unit is perpendicular to the surface of liquid is shown in FIGS. 10A and 10B. The imaging unit is arranged obliquely to the long axis of the capsule endoscope. In this condition, by setting the position of the center of gravity of the capsule endoscope so as to satisfy the above conditions (see FIGS. 8A, 8B, 9A and 9B), the direction of the optical axis of the imaging unit in liquid can be arranged to be perpendicular to the surface of liquid.

Next, a capsule endoscope that floats in liquid introduced inside a body and for which the specific gravity, the position of the center of gravity, and the position of the imaging unit are set such that the surface of water does not enter inside the boundary of the field of view and inside of the illumination boundary is shown in FIGS. 11A and 11B. The specific gravity of the capsule endoscope to the liquid introduced inside the body is indicated by ρ. The volume of the capsule endoscope is divided to be in a ratio of ρ:1−ρ to define a plane that does not have an intersecting part that intersects with the boundary of the field of view and the illumination boundary outside the capsule endoscope. When the center of gravity of the capsule endoscope is far from this plane than the center of the volume of the portion in which the volume ratio is ρ, and when a straight line that connects the center of gravity of the capsule endoscope and the center of the volume of the portion in which the volume ratio is ρ is perpendicular to the plane, the capsule endoscope floats on the surface of the liquid in a state where the surface of water does not enter inside the boundary of field of view and the illumination boundary. At this time, the surface of water is on the same plane as the plane described above.

The principle that the capsule endoscope floats in this state is the same as that in the case shown in FIGS. 9A and 9B described above.

By setting the specific gravity of the capsule endoscope, the position of the center of gravity, the position of the imaging unit so as to satisfy the above conditions, a capsule endoscope that floats in a state where the surface of water does not enter inside the boundary of field of view and inside the illumination boundary can be achieved for certain.

It is possible to prevent entrance of the reflection light from the surface of water into the field of view, and reduction of the amount of light due to reflection of the illumination light on the surface of water. Therefore, a further clear image can be acquired.

Furthermore, a modification of a capsule endoscope that floats in liquid introduced inside a body, and for which the specific gravity, the position of the center of gravity, and the position of the imaging unit are set such that the surface of water does not enter inside the field of view and inside the illumination boundary is shown in FIGS. 12A and 12B. The imaging unit is arranged obliquely to the long axis of the capsule endoscope. In this condition also, by setting the position of the center of gravity of the capsule endoscope so as to satisfy the same conditions (see FIG. 5) as that in the case of the second embodiment described above, the capsule endoscope can float on the surface of liquid in a state where the surface of water does not enter inside the boundary of the field of view and inside the illumination boundary.

Figure 13:
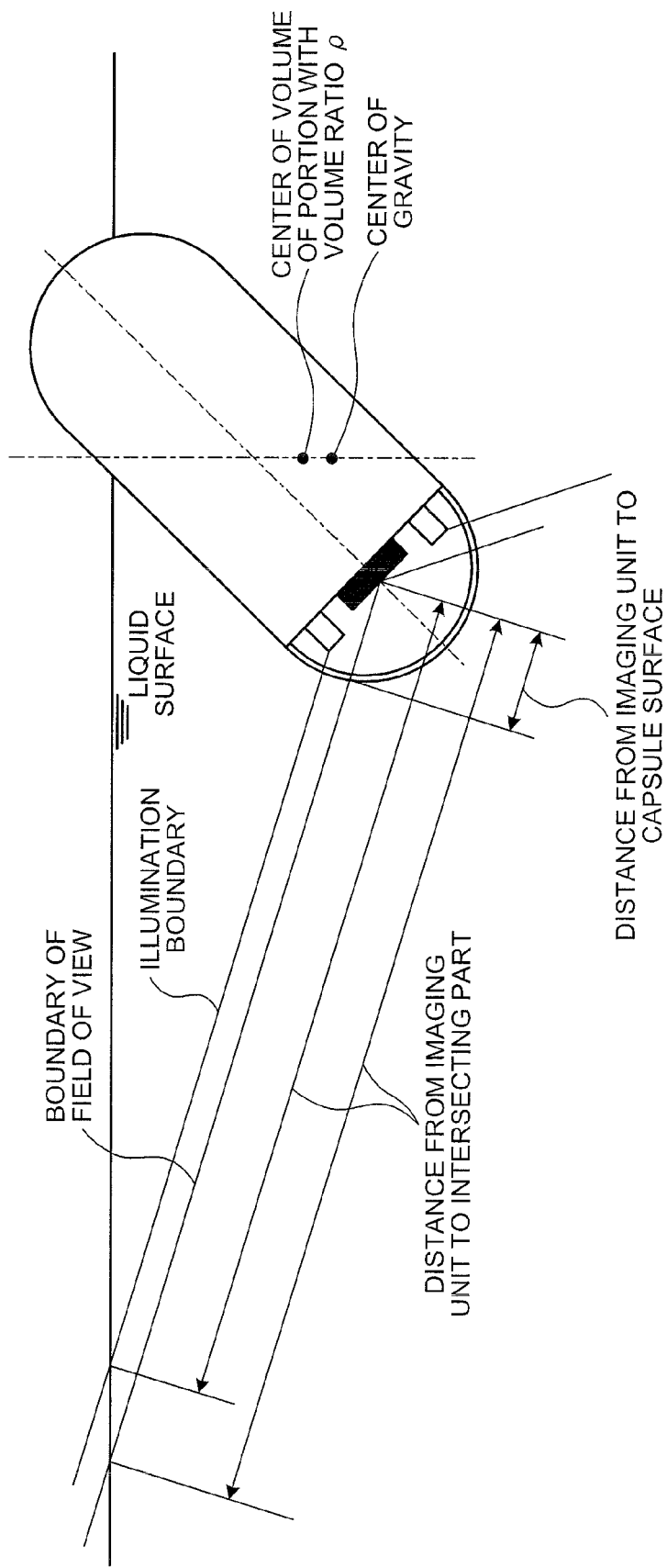
FIG. 13 is a schematic diagram showing a capsule endoscope in which the boundary of a field of view or an illumination boundary intersects with the surface of liquid at a point sufficiently far from a capsule-shaped casing.

Although it is desirable that the surface of water do not enter inside the boundary of the field of view and inside the illumination boundary, as shown in FIG. 13, a clear image can be acquired also when the capsule endoscope has the intersecting part at a position having sufficient distance from the capsule endoscope.

When the surface of water enters inside the boundary of the field of view and inside the illumination boundary at a point sufficiently far away, the amount of light at the surface of water is sufficiently small, and therefore, there is little influence of the reflection occurring on the surface of water. Furthermore, there is high possibility that a wall of an intestine is present at a closer point than a point where the surface of water intersects with the boundary of the field of view and the illumination boundary, and therefore, the possibility that the surface of water is included in an image is remarkably low.

The amount of light decreases inversely with the square of the distance. Therefore, when the distance to the surface of water is equal to or more than 3.2 times as long as the distance from the imaging unit to the surface of a capsule (outer surface of the capsule endoscope), the amount of light has decreased to about $\frac{1}{10}$. Accordingly, it can be considered that the influence of the reflection of light decreases to $\frac{1}{10}$ or lower.

As described above, when the capsule endoscope has the intersecting part at a point far away having a distance 3.2 times as long as the distance from the imaging unit to the surface of the capsule, the capsule endoscope can acquire a clear image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A capsule endoscope comprising:
a capsule-shaped casing;
a first imaging unit and a second imaging unit that are arranged inside the capsule-shaped casing in a fixed manner, the first imaging unit being arranged at one end portion of the capsule-shaped casing in a longitudinal direction of the capsule-shaped casing, and the second imaging unit being arranged at another end portion of the capsule-shaped casing, the capsule endoscope taking an image of an inside of an organ by the first imaging unit and the second imaging unit in a state where the capsule endoscope is floating in liquid that is introduced inside the organ of a subject; and a first illuminating unit that illuminates an imaging field of view of the first imaging unit and a second illuminating unit that illuminates an imaging field of view of the second imaging unit, wherein specific gravity of the capsule endoscope to the introduced liquid is $\rho$ wherein ($\rho<1$), a plane divides the capsule endoscope such that a volume ratio is to be $\rho:1-\rho$, a straight line that connects a center of volume and a center of gravity of the capsule endoscope is substantially perpendicular to the plane, and the center of gravity is present at a position farther distant from the plane than the center of volume, and a surface of a boundary of a field of view that forms an angle of view of the first imaging unit and the plane do not intersect with each other outside the capsule endoscope, a surface of a boundary of a field of view that forms an angle of view of the second imaging unit and the plane do not intersect with each other outside the capsule endoscope, a first optical axis of the first imaging unit intersects with a surface of a portion whose volume ratio is $1-\rho$ that is obtained by dividing the capsule endoscope by the plane, a second optical axis of the second imaging unit intersects with a surface of the portion whose volume ratio is $\rho$ that is obtained by dividing the capsule endoscope by the plane, optical characteristics of the first imaging unit are different from those of the second imaging unit, and a light emitting amount of the first illuminating unit is different from that of the second illuminating unit.

2. The capsule endoscope according to claim 1, wherein the plane and at least one of the first optical axis of the first imaging unit and the second optical axis of the second imaging unit are substantially perpendicular to each other.

3. The capsule endoscope according to claim 1, wherein the first optical axis of the first imaging unit and the second optical axis of the second imaging unit are substantially parallel to each other.

4. The capsule endoscope according to claim 1, further comprising an optical member for each of the first and second imaging units to image an object, wherein a transparent water-drop protective film is formed on an outer surface of the optical member.

5. The capsule endoscope according to claim 4, wherein the transparent water-drop protective film is any one of a water-repellent film and a hydrophilic film.

6. The capsule endoscope according to claim 1, wherein a distance between the first imaging unit and a focal point of the first imaging unit is longer than a distance between the second imaging unit and a focal point of the second imaging unit, and the light emitting amount of the first illuminating unit is larger than that of the second illuminating unit.

* * * * *